(12) United States Patent  
Carver et al.

(10) Patent No.: US 7,780,733 B2
(45) Date of Patent: Aug. 24, 2010

(54) ARTIFICIAL SPINAL DISC REPLACEMENT SYSTEM AND METHOD

(76) Inventors: Donna Jean Carver, 1100 Saddle Ct., Mansfield, TX (US) 76063-5730; Chad Anthony Barrie, 3904 San Luis CT, Arlington, TX (US) 76016-2741; John David Herrera, 9118 Post Oak Ct., Arlington, TX (US) 76002-5009

( * ) Notice: Subject to any disclaimer, the term of this patent is extended or adjusted under 35 U.S.C. 154(b) by 115 days.

(21) Appl. No.: 12/319,309

(22) Filed: Jan. 6, 2009

(65) Prior Publication Data

US 2009/0132049 A1   May 21, 2009

Related U.S. Application Data

(62) Division of application No. 11/544,136, filed on Oct. 9, 2006, now Pat. No. 7,491,240.

(60) Provisional application No. 60/725,460, filed on Oct. 10, 2005.

(51) Int. Cl.
*A61F 2/44* (2006.01)

(52) U.S. Cl. .................. 623/17.13; 623/17.15; 606/279

(58) Field of Classification Search ............. 623/17.11, 623/17.12, 17.13, 17.14, 17.15, 17.16; 606/246, 606/249, 279; 403/96, 98
See application file for complete search history.

(56) References Cited

U.S. PATENT DOCUMENTS

| | | | |
|---|---|---|---|
| 5,246,458 A | 9/1993 | Graham | |
| 5,534,031 A | 7/1996 | Matsuzaki et al. | |
| 5,693,100 A | 12/1997 | Pisharodi | |
| 5,755,796 A | 5/1998 | Ibo et al. | |
| 5,776,196 A | 7/1998 | Matsuzaki et al. | |
| 5,776,198 A | 7/1998 | Rabbe et al. | |
| 5,899,941 A | 5/1999 | Nishijima et al. | |
| 6,146,421 A | 11/2000 | Gordon et al. | |
| 6,179,874 B1 | 1/2001 | Cauthen | |
| 6,402,750 B1 | 6/2002 | Atkinson et al. | |
| 6,458,159 B1 | 10/2002 | Thalgott | |
| 6,517,580 B1 | 2/2003 | Ramadan et al. | |
| 6,602,257 B1 | 8/2003 | Thramann | |
| 6,736,815 B2 | 5/2004 | Ginn | |
| 7,052,515 B2 * | 5/2006 | Simonson ................ 623/17.13 |
| 7,309,357 B2 | 12/2007 | Kim | |
| 7,713,304 B2 * | 5/2010 | Ankney et al. ........... 623/17.16 |
| 2003/0083749 A1 | 5/2003 | Kuslich et al. | |
| 2004/0102849 A1 | 5/2004 | Ralph et al. | |

(Continued)

*Primary Examiner*—Eduardo C Robert
*Assistant Examiner*—Jan Christopher Merene
(74) *Attorney, Agent, or Firm*—Kevin Mark Klughart

(57) ABSTRACT

An artificial spinal disc implant method for intervertebral disc replacement (0810) is disclosed which is formed from an upper (0801) and lower (0802) bracket which mate to upper and lower spinal vertebrae via upper (0831) and lower (0832) vertebral contact surfaces on the upper (0801) and lower (0802) brackets. The upper (0801) and lower (0802) brackets are joined together via springs (0811) connected to the upper bracket (0801) which rest in spring guide tracks (0812) on the lower bracket. The springs (0811) are connected to the upper bracket (0801) via the use of spring fasteners (0821, 0822). The upper (0801) and lower (0802) brackets may be installed in sections (0851, 0861, 0871, 0852, 0862, 0872) using laparoscopic surgical techniques and are attached to upper/lower spinal vertebrae respectively via adhesive means applied using injection holes/ports (0841, 0842) in the upper (0801) and lower (0802) brackets respectively.

19 Claims, 40 Drawing Sheets

U.S. PATENT DOCUMENTS

2004/0199253 A1 10/2004 Link et al.
2004/0210218 A1 10/2004 Dixon et al.
2005/0251260 A1* 11/2005 Gerber et al. ............ 623/17.13
2006/0052872 A1 3/2006 Studer et al.
2006/0200243 A1 9/2006 Rothman et al.
2008/0071375 A1* 3/2008 Carver et al. ............. 623/17.13
2008/0077246 A1 3/2008 Fehling et al.

* cited by examiner

*Prior Art*

*Prior Art*

*Prior Art*

1200

1600

1800

2100

2200

2600

3000

3200

3300

3400

3500

3600

3700

3800

3900

ARTIFICIAL SPINAL DISC REPLACEMENT SYSTEM AND METHOD

CROSS REFERENCE TO RELATED APPLICATIONS

This application is a DIVISIONAL Utility patent application subsequent to parent utility patent application Ser. No. 11/544,136 for "ARTIFICIAL SPINAL DISC REPLACEMENT SYSTEM AND METHOD", filed on Oct. 9, 2006, now U.S. Pat. No. 7,491,240 published Feb. 17, 2009.

Applicant claims benefit pursuant to 35 U.S.C. §119 and hereby incorporates by reference Provisional patent application for "ARTIFICIAL SPINAL DISC REPLACEMENT SYSTEM AND METHOD", Ser. No. 60/725,460, filed Oct. 10, 2005, and submitted to the USPTO with Express Mail on Oct. 10, 2005 with tracking number ER618466616US.

Applicant claims benefit pursuant to 35 U.S.C. §120 and hereby incorporates by reference Utility patent application for "ARTIFICIAL SPINAL DISC REPLACEMENT SYSTEM AND METHOD", Ser. No. 11/544,136, filed Oct. 9, 2006, and submitted to the USPTO with Express Mail on Oct. 9, 2006 with tracking number ER618466616US.

PARTIAL WAIVER OF COPYRIGHT

All of the material in this patent application is subject to copyright protection under the copyright laws of the United States and of other countries. As of the first effective filing date of the present application, this material is protected as unpublished material.

However, permission to copy this material is hereby granted to the extent that the copyright owner has no objection to the facsimile reproduction by anyone of the patent documentation or patent disclosure, as it appears in the United States Patent and Trademark Office patent file or records, but otherwise reserves all copyright rights whatsoever.

STATEMENT REGARDING FEDERALLY SPONSORED RESEARCH OR DEVELOPMENT

Not Applicable

REFERENCE TO A MICROFICHE APPENDIX

Not Applicable

FIELD OF THE INVENTION

The field of the present invention relates to the use of artificial spinal disc replacements, including systems and methods associated with same, and generally includes apparatus associated with United States Patent Classification 623/17.16 and methods of installing these apparatus on patients.

DESCRIPTION OF THE PRIOR ART

Artificial Disc Replacement Revision

In a recent study, (a multi-center prospective clinical trial of 688 patients, 375 of whom were randomized to receive either a artificial disc or a single level lumbar spinal fusion), although the rate of revision was 2% lower in the artificial disc, the results showed that a revision may still be necessary in an artificial disc replacement nearly as often as it is in traditional spinal fusion surgery.

In clinical trials (one 2-year study recently presented to the FDA panel) comparing artificial disc replacement to spinal fusion surgery, results have already proven that artificial disc patients were able to maintain flexibility, experienced improvements in pain and functional ability, required shorter hospital stays, and had greater satisfaction with the outcome of their procedure.

Current State of the Art (0100, 0200)

There are currently several types of artificial disc replacements on the U.S. market. Some of these artificial discs are known as the Charite, Prodisc, Maverick, and the Bryan. There have been other artificial discs in the past (such as the Acroflex), but those have suffered distressing failure for the patients. Examples of the present state of the art in spinal disc replacements are generally illustrated in FIG. 1 (0100) extracted from U.S. Pat. No. 6,764,512 issued to Arnold Keller on Jul. 20, 2004 for PLASTIC IMPLANT WITH CHANNEL FOR RADIOGRAPHIC CONTRAST WIRE, and FIG. 2 (0200) extracted from U.S. Pat. No. 6,726,720 issued to Raymond Ross, Michael O'Neal, and Mark Boomer on Apr. 27, 2004 for MODULAR DISC PROSTHESIS. FIG. 2 (0200) is commonly referred to as the Charite spinal disc replacement, and is widely used in the arena of spinal disc replacement.

Prior Art Surgical Procedures (0300)

The current procedure for performing the artificial disc replacement is typically done with two surgeons, working together. A general or vascular surgeon approaches the spine through and incision in the abdomen (as generally illustrated in FIG. 3 (0300)) and carefully moves internal organs and blood vessels out of the way (0311) to provide access to the spine (0301). Then a spine surgeon uses special tools to remove the damaged disc and creates a space between the two vertebrae for the implantation of the artificial disc. The procedure general takes one to two hours, and as illustrated in FIG. 3, is highly invasive and subjects the patient (0310) to risks of infection and other surgical complications.

In a spinal fusion surgery, the damaged disc is removed and the vertebrae are joined together using bone grafts and metal screw and/or cages so that motion can no longer occur in this area of the spine. Often times with spinal fusion surgery, the bone graft used to pack the disc space is bone that the surgeon has to remove from the patient's hip. This means that the patient ends up having two incisions, the second one being over the superior crest of the ileum where the bone is harvested (scraped off). During recovery, the patient may experience pain in the hip at the harvest site. Patients usually have to wear a brace for about three months after surgery and may need to be fitted with a bone stimulator to promote healing at the fusion site.

BACKGROUND OF THE INVENTION

Overview (0300)

An intervertebral ("spinal") disc as generally illustrated in FIG. 3 (0301) performs several functions including maintaining normal intervertebral height ("spacer"), absorbing and transferring forces of spinal disturbances ("shock absorber") and a fulcrum of motion. A normal intervertebral disc is comprised of a gelatinous central portion called the nucleus pulposus and surrounded by an outer ligamentous ring called the annulus fibrosus. The gelatinous nuclear material directs the forces of axial loading outward and the annular fibers help distribute that force. The annulus fibrosus has overlapping radial bands to "seal" the nucleus and allow intradiscal pressures to rise as the disc is loaded, as well as allow torsional stresses to be distributed through the annulus under normal loading without rupture.

Unfortunately, injury to the spine or spinal discs is a common occurrence in the workplace, resulting in significant pain and suffering for patients so afflicted. About 65 million Americans suffer from low back pain every year, according to the American Association of Neurological Surgeons (AANS). Americans spend about USD$50 billion each year on low back pain, which represents the most common cause of job-related disability and lost work days in the United States. More than 12 million people are reported to have degenerative disc disease and more than 200,000 have lumbar spinal fusion surgery every year. Lumbar spinal fusion surgery is a common surgical treatment for low back pain or degenerative disc disease and is often effective in reducing pain, but it limits range-of-motion (ROM) and may transfer extra stress to discs above and below the fusion site.

Spinal Disc Injury Overview

The vertebral column has 24 individual vertebrae arranged in cervical, thoracic and lumbar regions. The sacral and coccygeal vertebrae are fused. The seven mobile cervical vertebrae support the neck and the (6-8 lb) head. The cervical spine is normally curved into lordosis. The twelve thoracic vertebrae support the thorax, head, and neck. They articulate with the 12 ribs bilaterally. The thoracic spine is curved into kyphosis. The five lumbar vertebrae support the upper body, torso and low back. The column of these vertebrae becomes curved at the onset of walking (1-2 years of age) into lordosis. The sacrum is the keystone of a weight bearing arch involving the hip bones. The vertebral curvatures may be affected (usually exaggerated) by posture, activity, obesity, pregnancy, trauma, and/or disease. A significant, possibly disabling, lateral curve of the spine which may occur for many reasons is called scoliosis.

The intervertebral disc consists of the annulus fibrosus (concentric interwoven collagenous fibers integrated with cartilage cells) attached to the vertebral bodies above and below, and the more central nucleus pulposus (a mass of degenerated collagen, proteoglycans and water). The discs make possible movement between the vertebral bodies. With aging, the discs dehydrate and thin, resulting in a loss of disc height. The cervical and lumbar discs, particularly, are subject to early degeneration from one or more of a number of causes. Weakening and/or tearing of the annulus can result in a broad-based bulge or a localized (focal) protrusion of the nucleus and adjacent annulus. As such, this event can compress a spinal nerve root.

Each pair of individual, unfused vertebrae constitutes a motion segment, the basic movable unit of the back. Combined movements of motion segments underlie movement of the neck and the middle and low back. Each pair of vertebrae in a motion segment, except C1-C2, is attached by three joints: a partly movable, intervertebral disc anteriorly, and a pair of gliding synovial facet (zygapophyseal) joints posteriorly. Ligaments secure the bones together and encapsulate the facet joints (joint capsules). The vertebral or neural canal transmits the spinal cord. The spinal cord is the lower extension of the central nervous system. It takes off from the medulla oblongata at the foramen magnum of the skull and ends as the conus medullaris at the vertebral level of L1 or L2. It bulges slightly in the lower cervical and lumbar segments where it gives off the roots of spinal nerves destined for the upper and lower limbs, respectively. The cord is ensheathed by three coverings (meninges): the inner pia mater, arachnoid, and the outer dura mater. The spinal cord is a center for spinal reflexes, a source of motor commands for muscles below the head, and a receiver of sensory input below the head. Located bilaterally between each pair of vertebral pedicles are passageways, each called intervertebral foramen, that are transmitting the spinal nerves from the spinal cord. Spinal nerves are collections of axons of sensory and motor neurons located in or adjacent to the spinal cord. Spinal nerves arise from nerve roots that come directly off the spinal cord. Thirty-one pairs of spinal nerves supply the body structure with sensory and motor innervation, except for those areas covered by the cranial nerves. From above to below, there are 8 cervical spinal nerves (C1-C8), 12 thoracic (T1-T12), 5 lumbar (L1-L5), 5 sacral (S1-S5), and one coccygeal (Co1).

The planes (orientation) of the articular facets determine the direction and influence the degree of motion segment movement. The plane of the cervical facets is angled coronally off the horizontal plane about 30 degrees. Considerable freedom of movement of the cervical spine is permitted in all planes (sagittal, coronal, horizontal). The thoracic facets lie more vertical in the coronal plane and are virtually non-weightbearing. The range-of-motion here is significantly limited in all planes, less so in rotation. The plane of the lumbar facets is largely sagittal, resisting rotation of the lumbar spine, transitioning to a more coronal orientation at L5-S1. The L4-L5 facet joints permit the greatest degree of lumbar motion in all planes.

Extension of the weight bearing joints is an anti-gravity function and extensor muscles of these joints tend to keep the standing body vertically straight. The center of gravity of an average human being standing with perfect posture is just anterior to the motion segment of S1-S2. Flexion of the neck and torso moves the center of gravity forward, loading the posterior cervical, thoracic and lumbar paraspinal extensor muscles. The muscles acting on the vertebral column, hip, knee and ankle joints make possible erect standing walking and running postures.

The deep muscles of the back and posterior neck extend, rotate or laterally flex one or more of the 24 paired facet joints and the 22 intervertebral disc joints of the vertebral column. The long muscles move several motion segments with one contraction, while short muscles can move one or two motion segments at a time. The erector spinae group comprises the principal extensors of the vertebral motion segments. Oriented vertically along the longitudinal axis of the back, they are thick, quadrilateral muscles in the lumbar region, splitting into smaller, thinner separate bundles attaching to the ribs, and upper vertebrae and head. Erector spinae arises from the lower thoracic and lumbar spines, the sacrum, ileum, and intervening ligaments. The transversospinalis group extends the motion segments of the back and rotates the thoracic and cervical vertebral joints.

These muscles generally run from the transverse processes of one vertebra to the spine of the vertebra above, spanning three or more vertebrae. The semispinales are the largest muscle of this group, reaching from mid-thorax to the posterior skull, the multifidi consist of deep fasciculi spanning 1-3 motion segments from sacrum to C2. The rotators are well defined only in the thoracic region. The small, deep-lying muscles cross the joints of only one motion segment. They are collectively major postural muscles. Electromyographic evidence has shown that these short muscles remain in sustained contraction for long periods of time during movement and standing/sitting postures. They are most prominent in the cervical and lumbar regions.

The neck is a complex tubular region of muscles, viscera, vessels and nerves surrounding the cervical vertebrae. The muscles of the neck are arranged in superficial and deep groups. The anterior and lateral muscle groups are divided into triangular areas by the sternocleidomastoid muscle. The posterolateral border is the trapezius muscle.

Biomechanical studies have shown that people bear load through the middle and posterior thirds of the disc. Spinal researchers have measured the amount of sliding and tilting at healthy spinal joints. During motions, the joint can be injured with stresses of only 6-7 kg and, in some cases, the disc could be injured and in others, a ligament might be injured. As our spine becomes older, it goes through certain changes related to its age through the process of simple wear and tear. The disc becomes thinner and more brittle and even cracked in places and they lose their elasticity and water content thus becoming less of a spinal stabilizer.

It is a prevalent misconception that most disc herniations result from a single event or trauma, microtrauma, primarily from repetitive flexion and rotation movement, leads to a degenerative cascade that frequently results in a herniated nucleus pulposus. While the clinical presentation of disc herniation varies because of the level size and position of the herniation, there are commons signs and symptom patterns that exist. About 80% of the population experience pain with radiation into the extremity along the anatomic distribution of the affected nerve root. Neural compression or irritation may precipitate motor weakness, reduced reflexes, and sensory loss. Compensatory posturing frequently occurs. About 90% of all lumbar disc herniations occur at the L4-L5 and L5-S1 levels.

Conservative treatment varies and includes traction, manual therapy techniques, electrotherapeutic modalities, other physical agents, dynamic muscular stabilization through physical therapy exercise, functional restorative education, and pharmacologic intervention (including oral or transdermal analgesics, NSAIDS, muscle relaxers, oral corticosteroids, and/or epidural steroids). Failure to respond to an active conservative treatment regimen for at least six weeks is just one of the indications for lumbar discectomy. Additional rationales for lumbar discectomy include severe, incapacitating pain that eludes all forms of medicinal and physical pain control measures, recurrent episodes of sciatica, significant neurologic deficit with significant positive straight leg raise test, bowel and bladder involvement, and progressive neurologic deficit are some of the strong indications for surgical intervention. The goals of rehabilitation are focused on return to maximal functional status and include reduction of pain frequency and intensity; maintenance of mobility; maximizing paraspinal strength, flexibility and conditioning; and prevention of recurrence of injury.

Discectomy via laminectomy is gradually being replaced by lumbar microdiscectomy as the standard of care for the surgical treatment of lumbar disc herniation. Other minimally invasive surgical techniques addressing lumbar disc herniation include percutaneous and endoscopic discectomy. Microdiscectomy offers advantages over the traditional laminectomy and discectomy by combining a smaller surgical exposure with far superior visualization of the operating field. Moreover, this less invasive surgical approach results in decreased perioperative bleeding and hematoma formation and less paraspinal muscle denervation and fibrosis. Improved visualization of the operating field allows for more precision in surgical technique, better nerve decompression, less chance of iatrogenic injury and a reduction in the amount of peridural scar tissue formed postoperatively. All these benefits lead to less postoperative pain and morbidity and a shorter hospital stay for the patient.

There has been a rapid evolution in the development and use of spinal fixation devices for lumbar spine fusion surgery. They are simply categorized as anterior or posterior fixation devices. The most common and most controversial fixation devices are the pedicle screw and rod/plate systems. Anterior fixation devices include screw and rod/plate systems as well as interbody cages. Essentially, these devices are hollow cylinders made of titanium, carbon, or bone. The cages are filled with autogenous bone graft and inserted between vertebral bodies. The patient's autogenous iliac crest is the standard source of bone graft material to fill the interbody cage. The goal of lumbar fusion is the union of two or more vertebrae. Most patients with interbody fixation become mobile and more independent than those with a non-instrumented spinal fusion, but the patients must wear a post-operative lumbar orthosis for an extended period and therefore require an extensive recovery time.

Different surgeons use different techniques to perform a lumbar fusion. The traditional approach is through a midline posterior incision. The posterior lumbar interbody fusion (PLIF) is a particularly demanding procedure associated with higher incidence of post-surgical nerve injuries than the posterolateral fusion. Some surgeons have moved to using an anterior approach (ALIF), but the ALIF cannot stand alone to withstand the forces of daily patient use and surgeons have found that, in order to prevent collapse or lack of fusion altogether, they have to protect the graft with posterior instrumentation which is placed either on the same day of surgery or in another procedure. A "360" circumferential fusion is also done in this manner.

OBJECTIVES OF THE INVENTION

Deficiencies in Prior Art Addressed

The common approach to stabilizing damaged or disrupted intervertebral discs is to fuse the vertebrae above and below the damaged disc. Although proven as a successful approach to permanently stabilize the injured area, fusion has the following drawbacks:

Fusion unnecessarily eliminates a portion of the spine's normal range-of-motion (ROM);

Fusion increases the stressors imposed on the adjacent mobile vertebra;

Fusion often causes subsequent breakdown of the intervertebral disc above and below the fused vertebrae;

Fusion causes osteophyte formation at the levels adjacent to the fusion;

Almost half of patients still have lumbar pain after the fusion procedure.

The present invention allows for preservation of the intervertebral disc space without immobilization of the vertebrae, thereby reducing the risk of breakdown of the adjacent vertebrae above and below and allowing full ROM at the level of the damaged disc.

By using special instrumentation and scopes with the present invention, implantation through laparoscopic spinal surgery requires only three to four small incisions, much like those a patient might experience when having another minor surgery such as a cholecystectomy or appendectomy. There are numerous benefits of this minimally invasive surgery versus surgical incisions made with traditional fusion surgery. The most significant benefit is a reduced hospital stay and reduced recuperation time.

Exemplary Invention Objectives

One skilled in the art will recognize that the present invention provides significant improvements to the patient as compared to the prior art. Accordingly, the objectives of the present invention are (among others) to circumvent the deficiencies in the prior art. Some of these benefits which may be present in some embodiments include (but are not limited to) the following objectives:

- To provide an ARTIFICIAL SPINAL DISC REPLACEMENT SYSTEM AND METHOD that overcomes the deficiencies in the prior art.
- Preservation of ROM in the patient.
- The replacement disc will remain secure without the need for screws into the spinal vertebrae.
- The procedure to install the invention may be laparoscopic, thereby alleviating the need for major patient surgery.
- The present invention will reduce the need for expensive post-operative care (physical therapy, hospital, physician visits, etc.).
- All repairs to the invention can be done laparoscopically.
- The present invention is modular and can be used in cervical or lumbar region and potentially thoracic regions of the spine.
- The present invention will rotate within limitations of the guide tracks.
- The present invention will allow bending of vertebrae for forward flexion, extension, and lateral flexion.
- The present invention can be made of any material that will allow for optimum spine function.
- The present invention can consist of brackets and spring design.
- The present invention brackets can be attached with an adhesive.
- The present invention upper bracket can have a protrusion which will be threaded to allow for efficient attachment of the spring assembly.
- The present invention spring assembly can be fully customizable for permanent ROM limitations if necessary due to physical limitations of existing vertebrae in the patient.
- The present invention springs can be altered for elasticity for acceptable movement.
- The present invention springs can be attached via specialized fasteners.
- The present invention disc replacement can consist of, but is not limited to, brackets and springs and nuts.
- The present invention can be used in osteoporotic, osteopenic, or normally aged bone.
- The present invention will not interrupt biomechanical alignment of the spine.
- The present invention can adjust the disc height to maintain intervertebral space, or increase or decrease this spacing.

One skilled in the art will recognize that this list of advantages is not exhaustive and may have application to some embodiments of the present invention and not others. While these objectives should not be understood to limit the teachings of the present invention, in general these objectives are achieved in part or in whole by the disclosed invention that is discussed in the following sections. One skilled in the art will no doubt be able to select aspects of the present invention as disclosed to affect any combination of the objectives described above.

BRIEF SUMMARY OF THE PRESENT INVENTION

Contrast with Prior Art

The common approach to stabilizing damaged or disrupted intervertebral discs is to fuse the vertebrae above and below the damaged disc. Although proven as a successful approach to permanently stabilize the injured area, fusion unnecessarily eliminates a portion of the spine's normal range-of-motion, increases the stressors imposed on the adjacent mobile vertebra, often causing subsequent breakdown of the intervertebral disc above and below the fused vertebrae, osteophyte formation at the levels adjacent to the fusion, and almost half of patients still have lumbar pain after the procedure. The present invention avoids these drawbacks of the prior art and preserves full ROM in the patient.

Overview (0400)

Artificial prosthesis have been commonly used to replace painful joints in hips and knees for more than 20 years and these are among the most successful and reliable operations performed today. Securing these replacements has been done with a variety of adhesives and/or bone glues. The present invention advances this concept forward by teaching a spinal disc replacement system that can be fixed to the spine vertebrae with adhesive using laparoscopic techniques (0401) as illustrated in FIG. 4 (0400).

Placement (0500, 0600, 0700)

The present invention relates generally to a spinal implant for use in intervertebral disc replacement. It is an articulating implant that restores proper intervertebral spacing, preserves spinal range-of-motion (ROM) and flexibility, and eliminates nerve root and/or spinal cord compression. As illustrated in FIG. 5 (0500), the present invention (0810) (with suitable modifications for size and placement) is applicable for use at any point (0501, 0502, 0503) along the spinal column (0510).

A more detailed depiction of the placement of the present invention in the spinal column is illustrated in FIG. 6 (0600), wherein the exemplary spinal disc replacement (0810) is inserted between an upper (0601) and lower (0602) vertebrae in the spinal column. As previously mentioned, the present invention is amenable for used at any point along the spinal column. It is an articulating implant that restores proper intervertebral spacing, preserves spinal ROM and flexibility, and eliminates nerve root and/or spinal cord compression.

Further detail of the present invention is generally illustrated in the perspective view of FIG. 7 (0700), wherein an exemplary embodiment (0810) is placed between two spinal vertebrae (0701, 0702). While a wide variety of invention embodiments is anticipated, the general placement as illustrated in FIG. 7 provides some insight into general application of the present invention.

General Assembly and Component Breakdown (0800)

The present invention is generally illustrated in the detailed exploded view of FIG. 8 (0800), wherein it is comprised of an upper bracket (0801), lower bracket (0802), and spring(s)

(0811) separating the brackets (0801, 0802). The present invention will allow for preservation of the intervertebral disc space without immobilization of the vertebrae, thereby reducing the risk of breakdown of the adjacent vertebrae above and below and allowing full ROM at the level of the damaged disc.

The upper bracket (0801) and lower bracket (0802) are generally not attached to the skeletal structure using screws as had been done by many of the other disc replacements on the market currently. Screws placed into fragile bone have the potential for breaking the bone and causing failure of the hardware/spinal replacement. Adhesive is much less invasive and has been proven successful many times over in hip and shoulder replacement surgeries worldwide. Upper (0831) and lower (0832) vertebral contact surfaces provide adhesion surfaces for adhesive to mate the upper/lower brackets to the corresponding upper/lower vertebrae. The upper/lower brackets are designed to include a hole in the bracket for adhesive/bone glue to be injected, as in item (0841).

The brackets as illustrated can be constructed of a variety of materials, including but not limited to titanium, chromium, cobalt, or a variety of plastics. Research indicates that many preferred exemplary embodiments employ material selection (optimally a titanium alloy) that is selected to support a spring specification of at least 1800 Newtons within the size of 3 to 8 mm spring width.

Additionally, as is illustrated in FIG. 8 (0800) and in other drawings, the system may be fabricated in multiple segments for the upper (0851, 0861, 0871) and lower (0852, 0862, 0872) brackets in a "jigsaw" or interlocking fashion to facilitate assembly within the context of a laparoscopic surgical procedure. The benefits of the modular design are that the disclosed spinal disc replacement can be placed in either cervical, thoracic, or lumbar areas and are adjustable for any body size.

BRIEF DESCRIPTION OF THE DRAWINGS

For a fuller understanding of the advantages provided by the invention, reference should be made to the following detailed description together with the accompanying drawings wherein.

Referring now in detail to the figures wherein like reference numbers like parts throughout, preferred forms of the present invention will now be described.

DESCRIPTION OF THE PRESENTLY PREFERRED EXEMPLARY EMBODIMENTS

Figure 1:
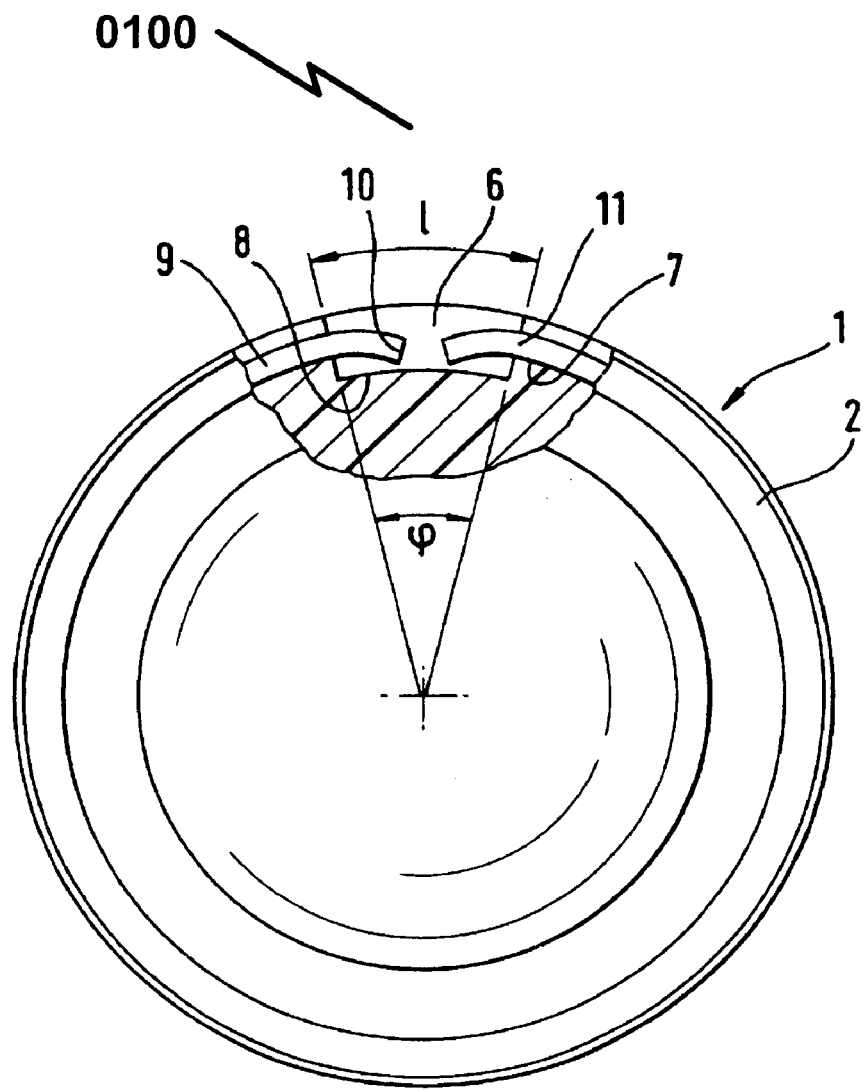
FIG. 1 illustrates a prior art embodiment of an artificial spinal disc implant extracted from U.S. Pat. No. 6,764,512 issued to Arnold Keller on Jul. 20, 2004 for PLASTIC IMPLANT WITH CHANNEL FOR RADIOGRAPHIC CONTRAST WIRE.
Figure 1:
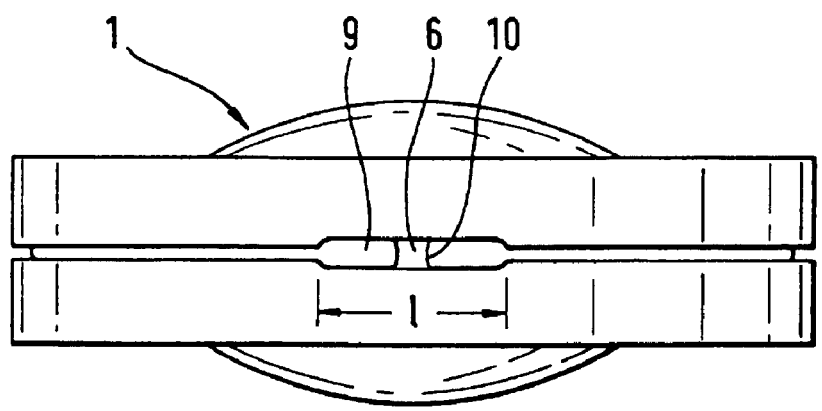
Figure 2:
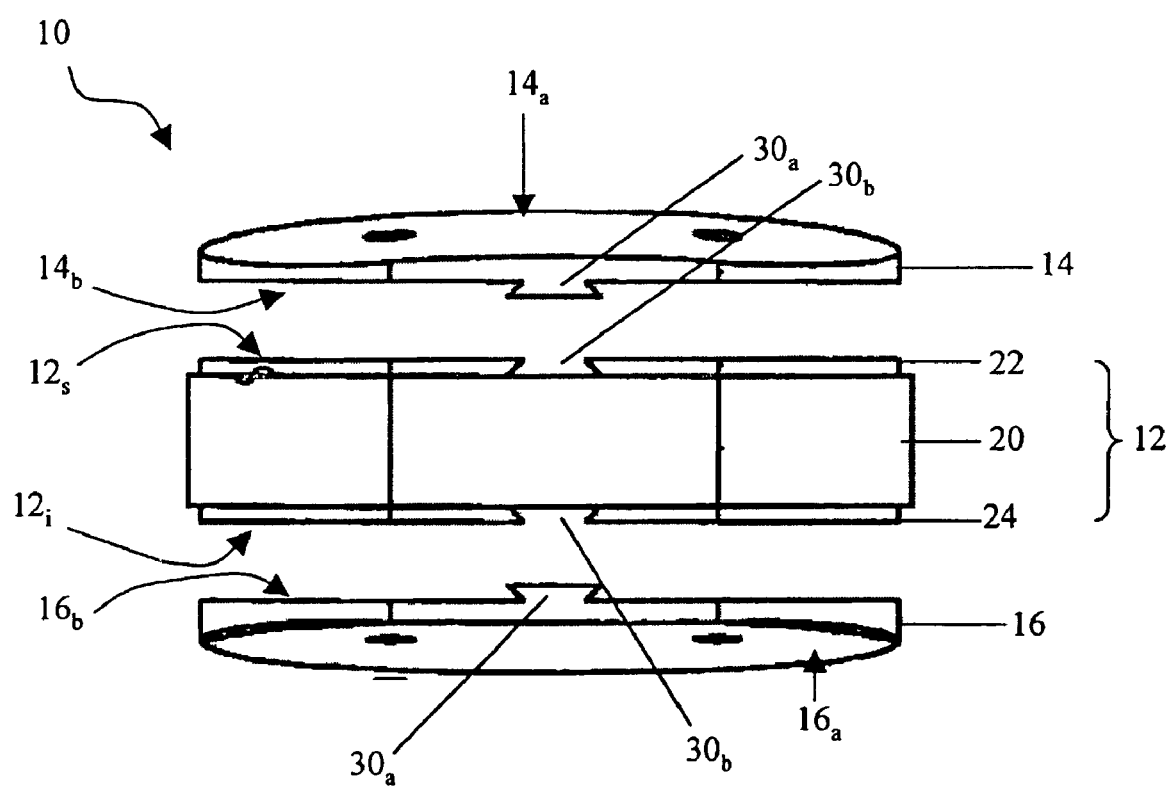
FIG. 2 illustrates a prior art embodiment of an artificial spinal disc implant extracted from U.S. Pat. No. 6,726,720 issued to Raymond Ross, Michael O'Neal, and Mark Boomer on Apr. 27, 2004 for MODULAR DISC PROSTHESIS.

While the present invention is susceptible of embodiment in many different forms, there is shown in the drawings and will herein be described in detailed preferred embodiment of the invention with the understanding that the present disclosure is to be considered as an exemplification of the principles of the invention and is not intended to limit the broad aspect of the invention to the embodiment illustrated.

The numerous innovative teachings of the present application will be described with particular reference to the presently preferred embodiment, wherein these innovative teachings are advantageously applied to the particular problems of an ARTIFICIAL SPINAL DISC REPLACEMENT SYSTEM AND METHOD. However, it should be understood that this embodiment is only one example of the many advantageous uses of the innovative teachings herein. In general, statements made in the specification of the present application do not necessarily limit any of the various claimed inventions. Moreover, some statements may apply to some inventive features but not to others.

Fastener Coatings not Limitive

While several preferred embodiments may incorporate special coatings on fasteners to promote integration into the spinal column or to promote self-locking of the fastener, the present invention scope is not limited by the specific fastener coatings listed herein.

Fastener Configuration not Limitive

In many preferred exemplary embodiments, the spinal implant disclosed herein may make use of a variety of fasteners for fixation of springs used between the upper/lower brackets. One skilled in the art will recognize that the exact fastener style may be determined by a variety of factors and is not necessarily limited to the exact configurations detailed herein. Fastener styles including but not limited to fastener head, fastener body, threading, recesses, locking mechanisms, and the like may be varied without loss of generality in the teachings of the present invention. Therefore, the term "fastener" or "fastening" should be given its broadest definition within the context of the teachings of the present invention.

Location not Limitive

The present invention is designed to be implemented as a spinal disc replacement, and within this context a variety of location placements within the spinal column are generally illustrated within this document. However, nothing within this description is intended to limit the scope of placement of the spinal disc replacement, and the teachings of the present invention may be applied (with appropriate structural modification to account for location) to placement within any portion of the patient's spinal column. The drawings and written description should not in any way limit the scope of where the invention may be applied with respect to placement within the spinal column.

Surface Conditioning not Limitive

In some preferred embodiments the vertebral contact surfaces are conditioned for advantageous adhesion between the contact surface and the associated spinal vertebrae via the use of adhesive or some other fastening means. While several exemplary methods of surface conditioning are illustrated herein, the scope of the invention is not limited by any specific method mentioned herein, as one skilled in the art can enumerate a variety of such methods.

Fastener Orientation not Limitive

Additionally, the present invention should not be limited in scope by the orientation of fasteners which are illustrated in the attached drawings and described herein. One skilled in the art will recognize that fastener orientation may in many circumstances be a preferential decision that is not directly tied to the function of the invention or the scope of the disclosed invention. As such, fastener orientation should not limit the invention scope.

Fabrication Materials not Limitive

The elements of this spinal implant can be fabricated from biocompatible materials including, without limitation, titanium, surgical alloys, stainless steel, chrome-molybdenum alloy, cobalt-chromium alloy, zirconium oxide ceramic, non-absorbable polymers, and other anticipated biocompatible metallic or polymeric materials. One skilled in the art will recognize that the teachings of the present invention are not limited by the type of material used in the manufacture of the disclosed spinal disc replacement.

Fixative not Limitive

In many preferred exemplary embodiments, the spinal implant disclosed herein makes use of an adhesive for fixation to adjacent vertebrae within the spinal column. One skilled in the art will recognize that the teachings of the present invention are not limited by the type of adhesive or fixative means used in the installation of the disclosed spinal disc replacement. While adhesive is clearly the preferred method of attachment in some preferred embodiments, one skilled in the art will recognize that other fixation means, including but not limited to screws, clasps, or other fixation means may be possible without limiting the teachings of the present invention.

Spring Fixation not Limitive

In many preferred exemplary embodiments, the spinal implant disclosed herein may make use of cylindrical threaded projections, bolts, nuts, or other fasteners for fixation of springs used between the upper/lower brackets. One skilled in the art will recognize that the teachings of the present invention are not limited by the means by which the springs are fastened to the upper or lower bracket. One skilled in the art will recognize that the spring feature taught by the present invention can also be integrated into the fabrication of the upper/lower bracket itself, with no loss of generality in the disclosed invention.

Component Part Count not Limitive

While the component count illustrated and discussed herein may be applicable to many preferred embodiments, the present invention anticipates that components may be sectioned or combined in many embodiments not illustrated.

Surface Coatings not Limitive

In many preferred exemplary embodiments, the spinal implant disclosed herein may make use of a variety of material coatings such as nylon, Teflon®, or other materials to reduce friction between moving parts or improve overall long term wear characteristics of the spinal implant. One skilled in the art will recognize that the teachings of the present invention are not limited by any surface coatings which may be applied to any of the components described by the teachings of the present invention.

Orientation not Limitive

In many preferred exemplary embodiments, the spinal implant disclosed herein comprises an upper bracket having springs which rest in spring guide tracks that are formed within a lower bracket, the upper/lower bracket structure being connected respectively to upper/lower vertebrae via vertebral contact surfaces on the upper/lower brackets. Note, however, that the orientation of the structure is not critical, and the orientation of the upper/lower bracket may be swapped such that the upper bracket contains the spring guide tracks and the lower bracket contains the springs.

Furthermore, one skilled in the art will recognize that while the present invention discloses a single spring guide track, the present invention may incorporate multiple spring guide tracks, and these tracks may reside on one or more of the upper/lower brackets. The present invention specifically anticipates situations in which the spring guide tracks are on both upper and lower brackets, with springs being placed to mate to these guide tracks on the bracket not containing the particular guide track.

Thus, the springs illustrated herein and their associated guide tracks may be replicated/mirrored with no loss of generality in the teachings of the present invention.

Spinal Interface not Limitive

In many preferred exemplary embodiments, the spinal implant disclosed herein may make use of an irregular spinal interface as generally illustrated in the drawings. One purpose of such an irregular interface is to promote adhesion to the spinal column when the system is fixed to the spinal column using adhesive. However, one skilled in the art will recognize that the teachings of the present invention are not limited by any particular surface interface as generally illustrated in the drawings, and that other spinal interface structures (including flat) may be suitable in some circumstances without departing from the teachings of the present invention.

Multi-Part Construction not Limitive

The present invention as illustrated herein may be comprised of an upper and lower bracket, with each of these assemblies being composed of a plurality of sections that are assembled together during a typical laparoscopic surgical procedure. While the examples illustrated herein comprise three upper bracket sections and three lower bracket sections, nothing within the scope of the present invention teachings limits the structure to this configuration. The upper/lower brackets may have one or more sectional pieces and may or may not be assembled within the patient during surgery.

Springs not Limitive

One skilled in the art will recognize that the springs detailed in this disclosure are illustrative only, and do not limit the scope of the claimed invention. "Spring" or "springs" in the context of this disclosure include any material or structure capable of absorbing shock, torsional stress, thrust, or extended wear. This definition includes the field of bearings and the like which are capable of supporting a range of rotational motion. Nothing in the present invention limits the scope to configurations with a plurality of springs, although many preferred embodiments exhibit multiple springs. One skilled in the art will recognize that a wide variety of materials consistent with the application of Hooke's Law can operate as a spring and would be applicable to the teachings of the present invention.

Spring Guide Tracks not Limitive

One skilled in the art will recognize that the spring guide tracks detailed in this disclosure are illustrative only, and do not limit the scope of the claimed invention. "Spring guide tracks" in the context of this disclosure include any material or structure capable of supporting and/or retaining a "spring" retained by the bracket not containing the spring guide track.

Nothing in the present invention limits the scope to configurations with a plurality of spring guide tracks, although many preferred embodiments exhibit multiple spring guide tracks. One skilled in the art will recognize a variety of methods by which a spring may rest in or be retained by a spring guide track, and the illustrations provided herein are only exemplary of the wide variety of methods by which this may be accomplished.

Surgical Technique not Limitive

In many preferred exemplary embodiments, the spinal implant disclosed herein may be installed using laparoscopic surgical techniques. However, one skilled in the art will recognize that the teachings of the present invention are not limited by any particular surgical technique, and that the present invention may be installed using a variety of surgical techniques without loss of generality in the teachings of the present invention.

Upper Bracket Construction not Limitive

In many preferred exemplary embodiments, the spinal implant disclosed herein may have an upper bracket structure further comprising springs, spring fasteners, and upper vertebral contact surface. The present invention specifically anticipates that this upper bracket structure may in some configurations combine as a unified structure the springs and spring fasteners within the context of the upper bracket. One skilled in the art will recognize that the upper bracket may be fabricated from material in which the springs are integrated into the product, eliminating the need for separate springs and/or spring fasteners.

Adhesive not Limitive

The terms "adhesive" and "adhesive agent" should be given broad definitions within the context of this disclosure. One skilled in the art will recognize that a variety of adhesive means are available for fixing the upper and/or lower brackets to their respective vertebrae, including but not limited to bone glue, bone cement, or other available bioadhesive substances. A particular adhesive may be chosen based on the embodiment of the present invention manufactured, as is well known in the art.

Edge Chamfering/Rounding not Limitive

The present invention detailed herein may incorporate in several preferred embodiments edge chamfering and/or rounding of edged to promote optimal operation of the spinal disc replacement and/or improved compatibility with insertion into the spinal column. One skilled in the art will recognize that the general concept of edge deburring and the like are well known in the art and may be applied to a wide scope of the teachings of the present invention, depending on the particular application. The scope of the present invention is not to be limited in any way by any examples of edge deburring, chamfering, rounding, or the like as illustrated herein.

Co-Planar Disc Structure not Limitive

The present invention may be implemented using co-planar upper/lower brackets as illustrated herein in some preferred exemplary embodiments. However, the invention may incorporate non-planar (non-co-planar) disc structures in which the upper and/or lower bracket is tapered rather than co-planar, permitting the replacement disc structure to more fully comport with the requirements of the replaced disc in the patient.

Therefore, nothing in the invention disclosure herein should be construed as limiting the scope of the present invention to co-planar upper and/or lower brackets. One skilled in the art will recognize situations in which non-co-planar upper and/or lower brackets are dictated by patient requirements.

General System Description (0800)

Figure 8:
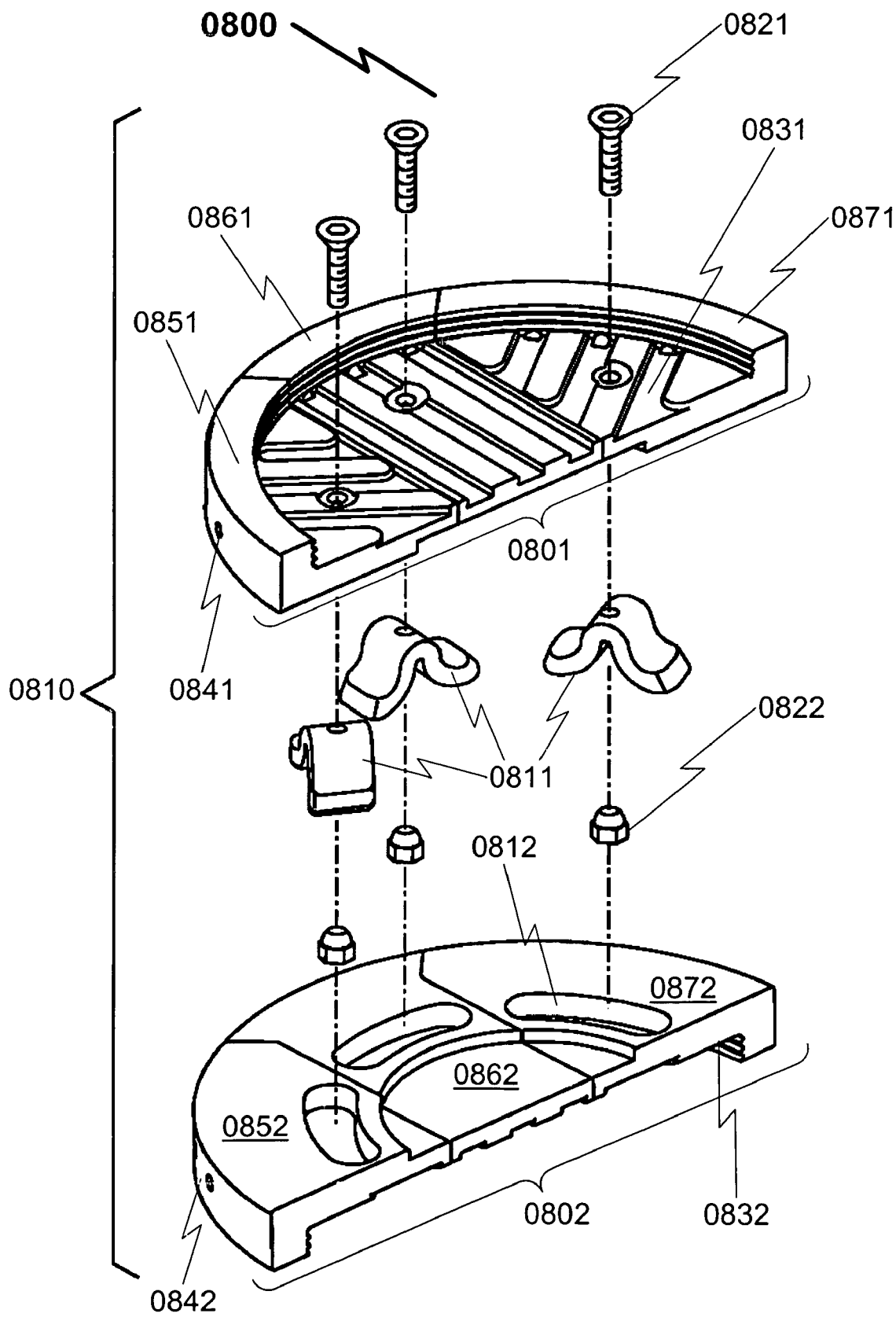
FIG. 8 illustrates a detail exploded view of a preferred exemplary embodiment of the present invention illustrating the major components of a typical embodiment of same.

As generally seen in FIG. 8 (0800), the general spinal disc replacement system comprises an upper bracket (0801), which further comprises spring(s) (0811), and vertebral contact surfaces (0831, 0832). The vertebral contact surfaces (0831, 0832) provides a permanent and rigid connection between the implant and the skeletal structure. The vertebral contact surfaces (0831, 0832) are in many preferred embodiments segmented (0851, 0861, 0871, 0852, 0862, 0872) for ease of installation and providing the ability to use laparoscopic surgical insertion. The upper bracket (0801) mates to a corresponding lower bracket (0802), which has one or more spring guide track(s) (0812) in which the spring(s) (0811) from the upper bracket (0801) ride and in which the springs (0811) are retained.

Fastening Means

While a wide variety of fastening means may be used to attach the spring(s) (0811) to the upper bracket (0801), several exemplary fastener types are illustrated in the drawings, including screws (0821) and nuts (0822). While recessed machine screws are preferred in some embodiments, one skilled in the art will recognize that a wide variety of other fastening means would be equally appropriate. One variation not illustrated in FIG. 8 (0800) would include the use of threaded cylindrical projections (studs) that are inserted into the upper bracket (0801) and onto which nut fasteners (0822) are attached to affect spring retention. The use of "shoulder bolts" or cylindrical fasteners with partial shaft threading is also specifically anticipated. One skilled in the art will recognize that this alternate form of cylindrical threaded projection could encompass a stud screwed into the upper bracket or some form of integrated machined threaded cylinder emanating from the upper bracket with no loss of generality in the teachings of the present invention.

Each individual segment of the vertebral contact surface may contain a cylindrical, threaded projection at it's midpoint on the inferior surface. The cylindrical, threaded projection may hold the nut upon application of the spring (0811). Also located at the midpoint but on the lateral surface are insertion holes on each segment. The three segments of the vertebral contact surface component of the upper bracket are meant to conjoin together to comprise the single unit of the upper bracket in some preferred embodiments. The upper/lower brackets extend from the outer edge of the skeletal structure to the interior, inferior surface of the vertebral body, but generally do not exceed the diameter of the vertebral body.

Either end of the vertebral contact surface (0831, 0832) will be angled toward the skeletal structure so that the surfaces are flush, making a cavity into which adhesive can be filled. The under surface of the bracket that contacts the skeletal surface can be textured/hatched to allow for maximum surface area to improve adhesion of the implant to the bone. The adhesive can be injected through the insertion holes (0841, 0842) on the lateral surface of each segment.

Perspective Installation Views (0900, 1000)

Figure 9:
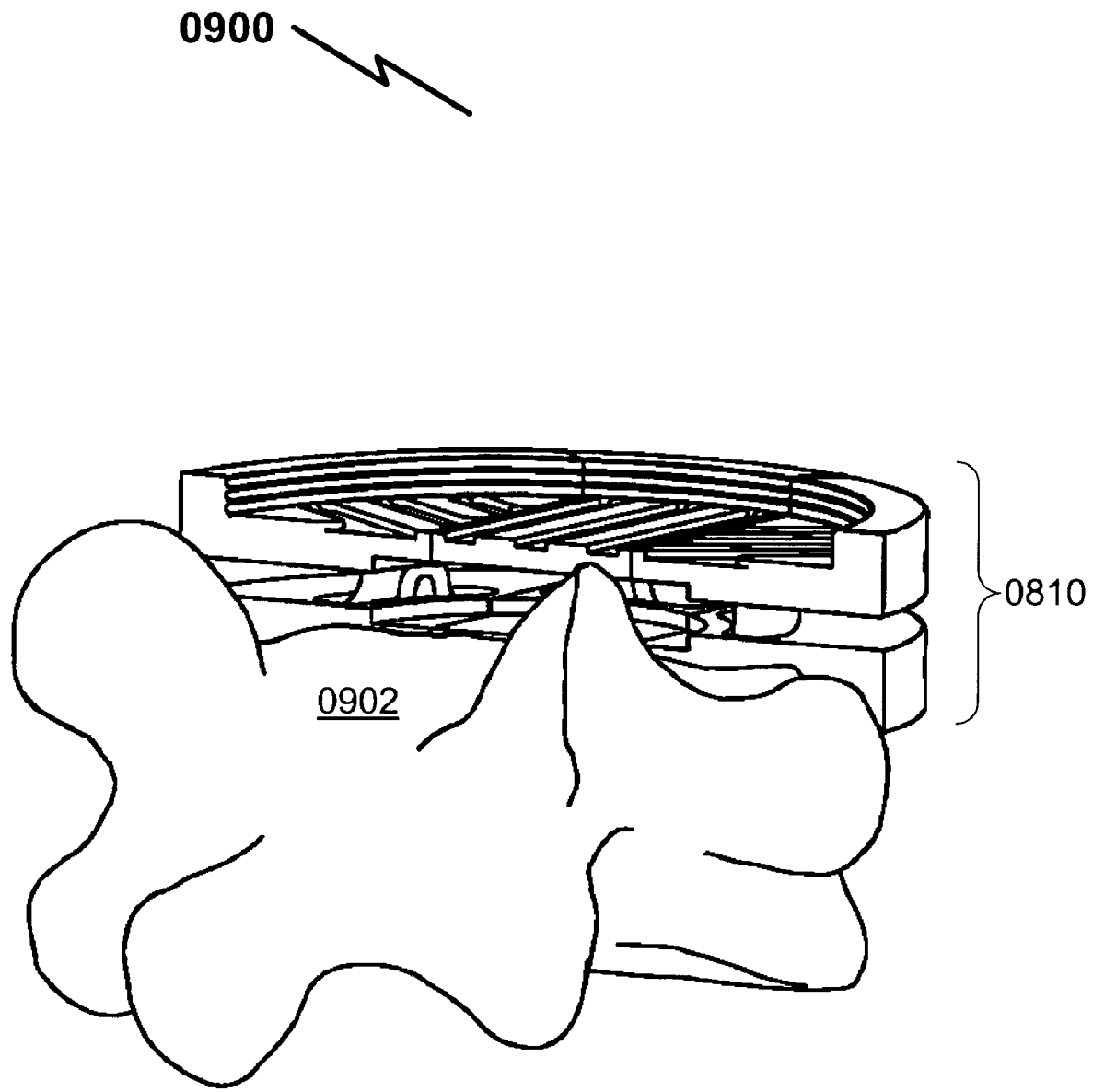
FIG. 9 illustrates a detail back side view of a preferred exemplary embodiment of the present invention as typically placed on a lower spinal vertebrae.
Figure 10:
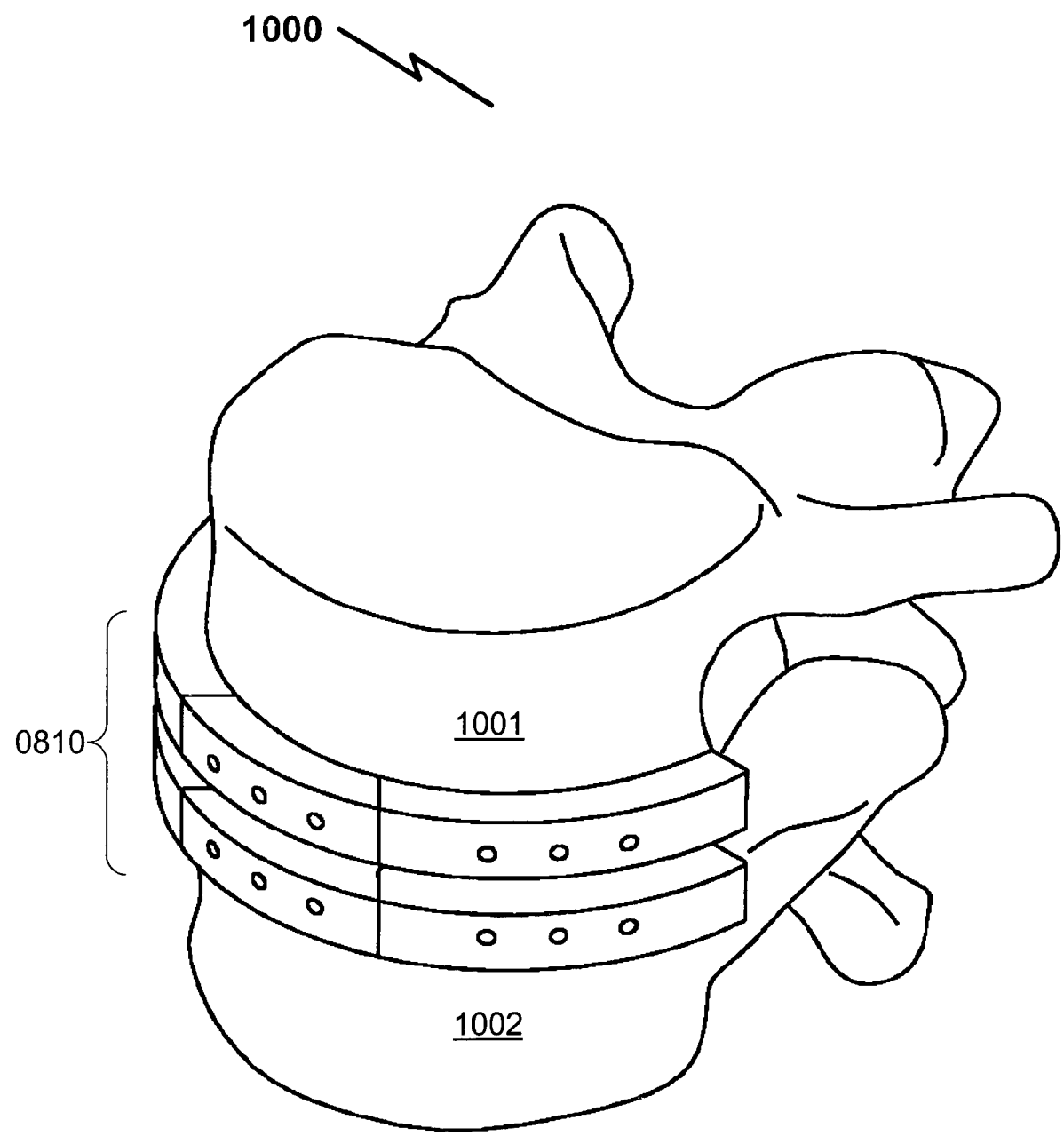
FIG. 10 illustrates a perspective view of a preferred exemplary embodiment of the present invention installed between two spinal vertebrae.

FIG. 9 (0900) and FIG. 10 (1000) provide perspective views of a presently preferred embodiment of the present invention (0810) as installed within the spinal column. FIG. 9 (0900) provides a patient-back perspective view of the present invention (0810) as it rests on the lower vertebrae (0902). FIG. 10 (1000) provides a perspective view of a presently preferred embodiment of the present invention (0810) as installed between an upper (1001) and lower (1002) vertebrae in a typical spinal column.

Perspective Component Views (1100, 1200, 1300, 1400, 1500)

Figure 11:
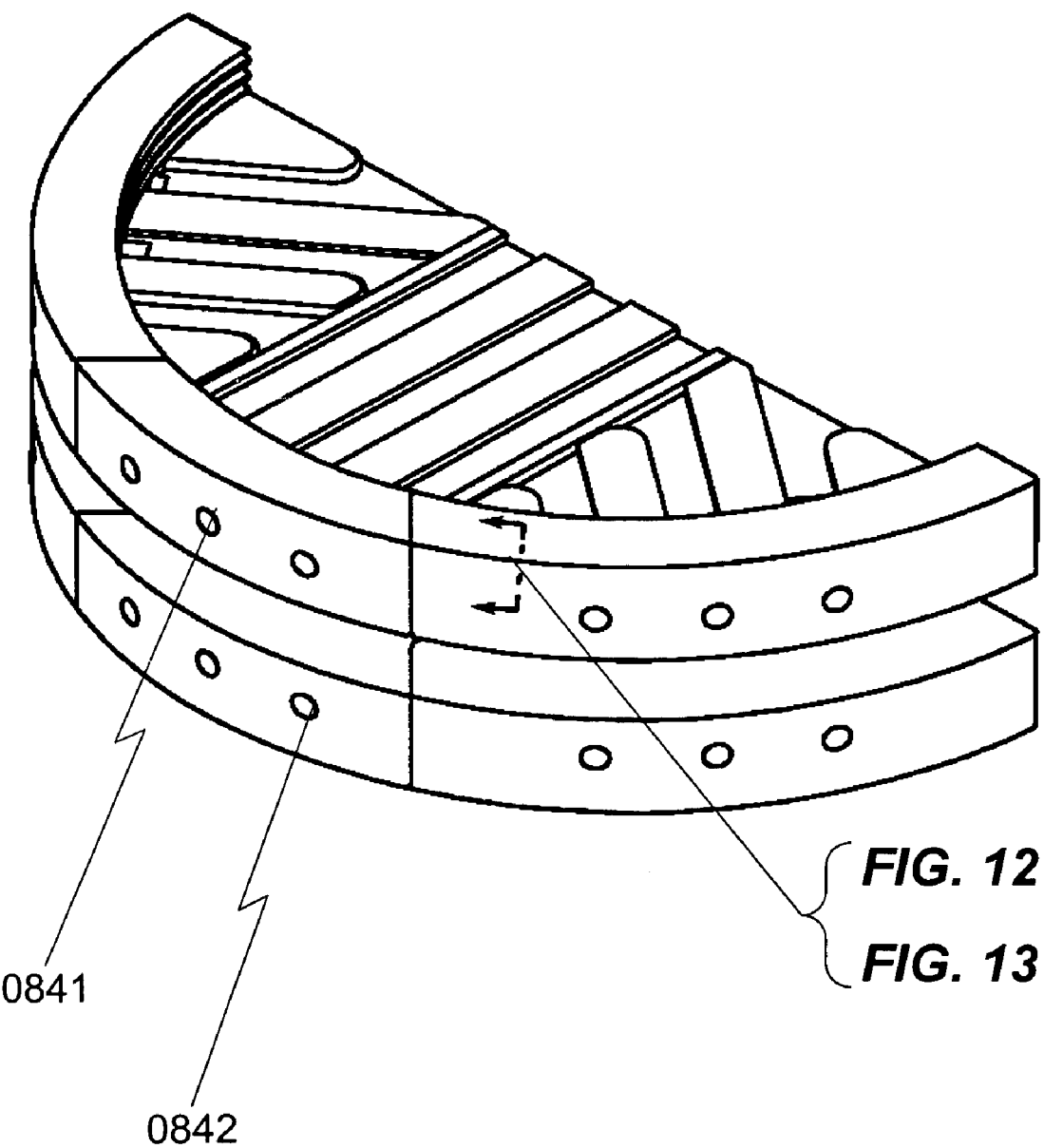
FIG. 11 illustrates a perspective view of a preferred exemplary embodiment of the present invention and details adhesive injection holes/ports on the upper and lower brackets.
Figure 12:
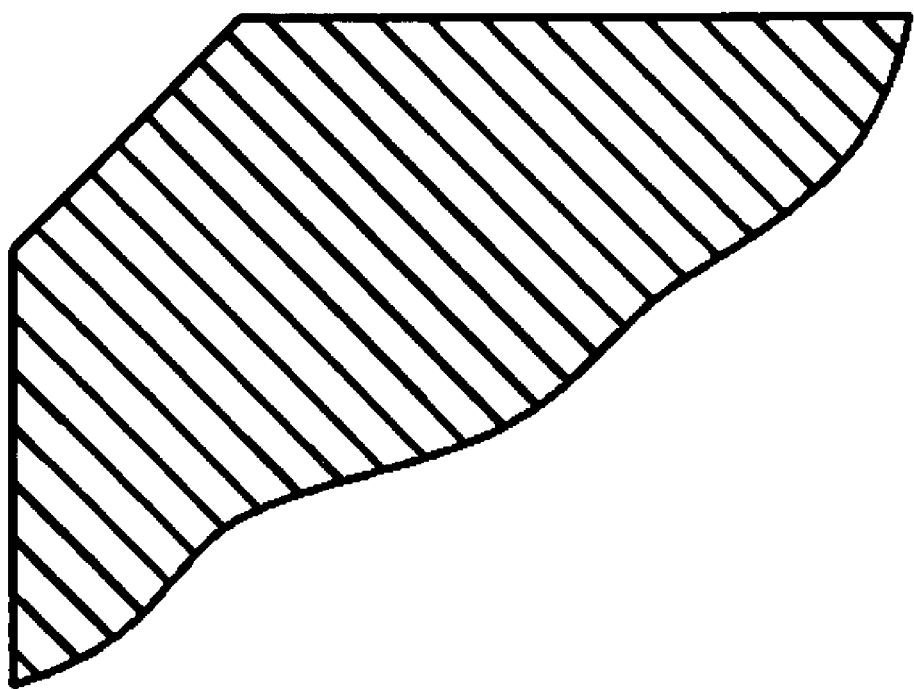
FIG. 12 illustrates an exemplary edge chamfer technique useful in manufacturing some preferred exemplary embodiments of the upper and/or lower bracket as taught by the present invention.
Figure 13:
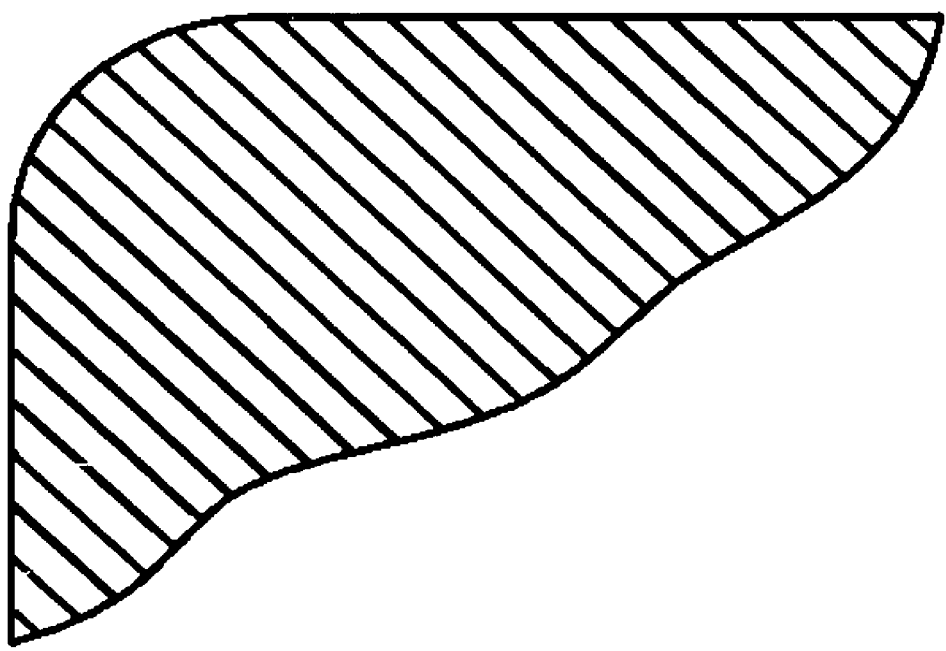
FIG. 13 illustrates an exemplary edge rounding technique useful in manufacturing some preferred exemplary embodiments of the upper and/or lower bracket as taught by the present invention.
Figure 14:
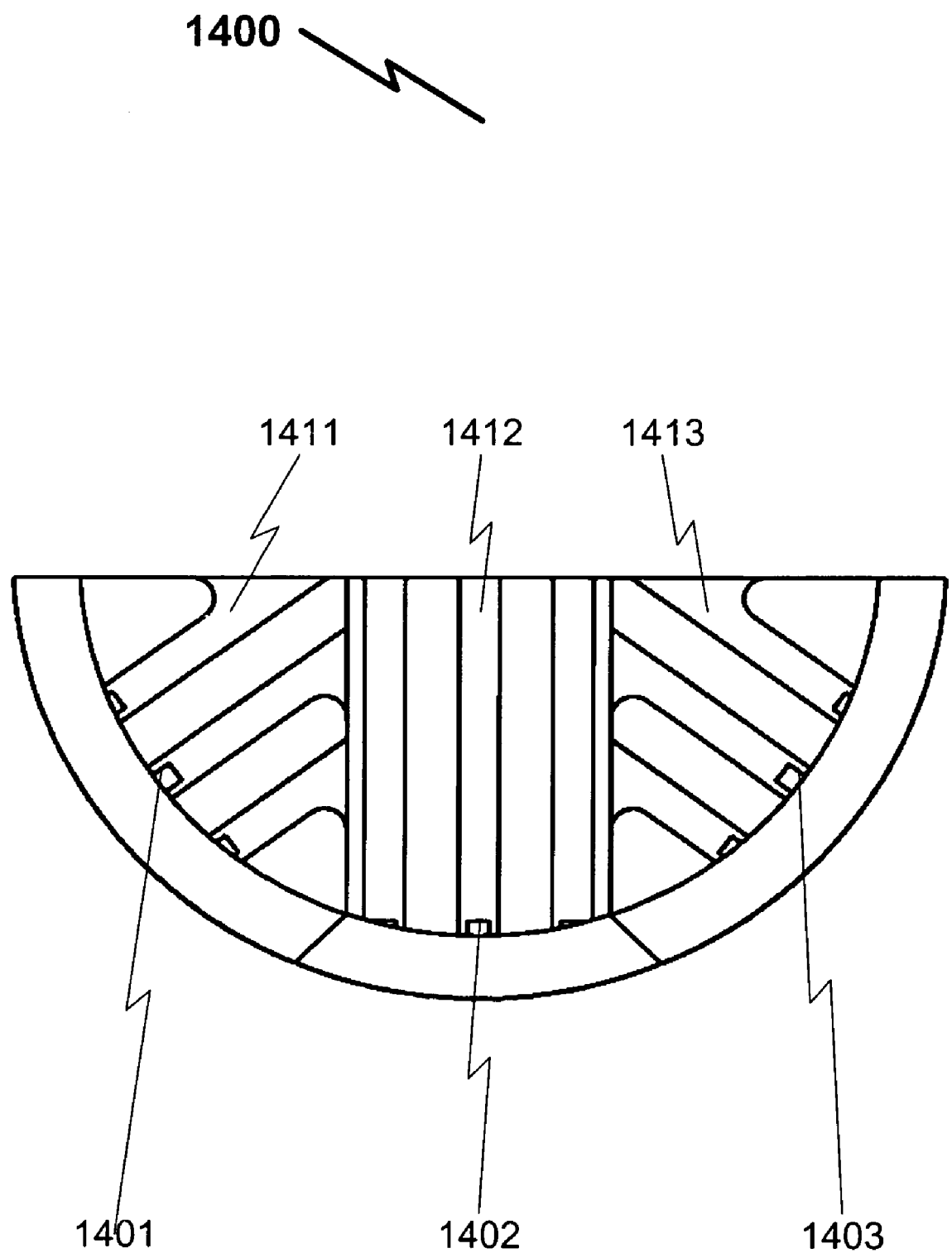
FIG. 14 illustrates a bottom view of a preferred exemplary embodiment of the present invention.
Figure 15:
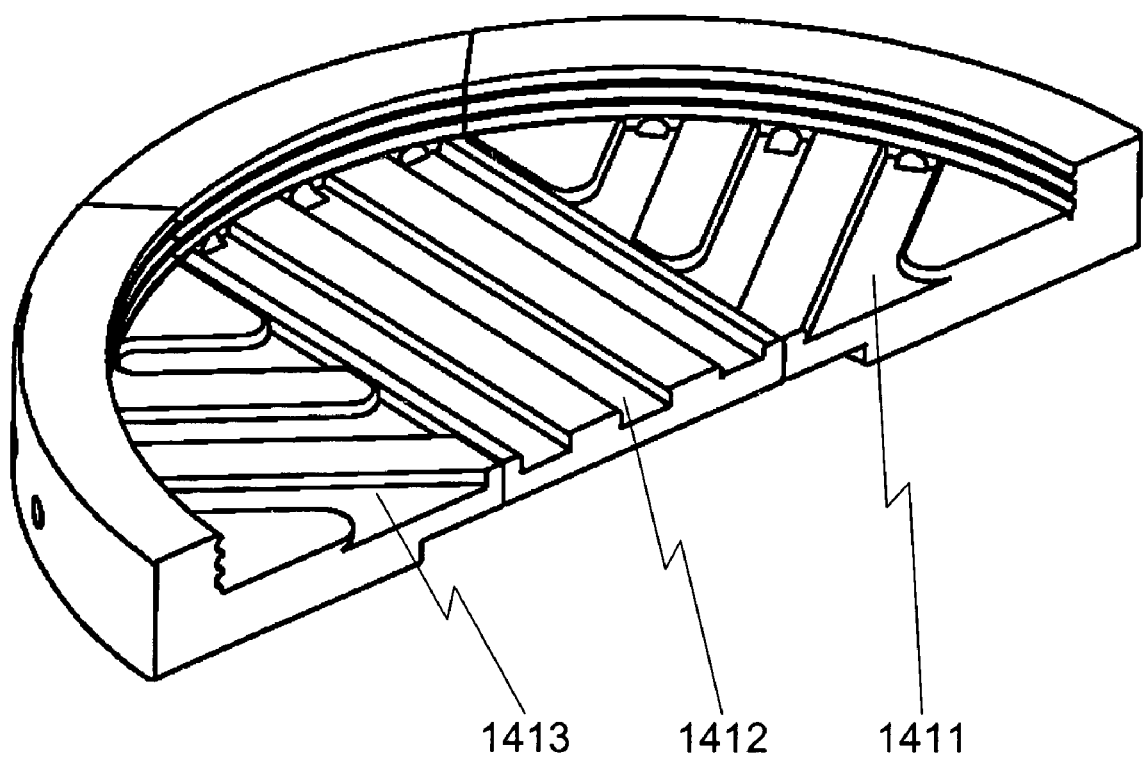
FIG. 15 illustrates a bottom perspective view of a preferred exemplary embodiment of the bottom bracket used in some embodiments of the present invention.

FIG. 11 (1100), FIG. 12 (1200), FIG. 13 (1300), FIG. 14 (1400), and FIG. 15 (1500), provide perspective component views of a presently preferred embodiment of the present invention (0810). These figures will now be discussed individually.

FIG. 11 (1100) illustrates a perspective view of a presently preferred embodiment of the present invention, and illustrates injection holes/ports for adhesive in the upper (0841) and lower (0842) bracket.

FIG. 12 (1200) and FIG. 13 (1300) illustrate cross sections of typical chamfering or rounding which may be implemented at the edges of any portion of the present invention to facilitate cohesive placement within the spinal column with minimum disruption of patient ROM. Note that one skilled in the art could apply the depicted chamfering/rounding or other well known edge detailing techniques to any portion of the upper and/or lower bracket structured depicted within this disclosure.

FIG. 14 (1400) and FIG. 15 (1500) illustrate perspective views of a presently preferred exemplary embodiment of the upper and/or lower bracket vertebral interfaces. These perspective views illustrate how the adhesive injection holes/ports (0841, 0842) as generally illustrated in FIG. 8 (0800) extend through the body (1401, 1402, 1403) of the brackets to form placement tracks (1411, 1412, 1413) for adhesive at the vertebral interfaces.

Upper Bracket Exploded Views (1600, 1700, 1800)

Figure 16:
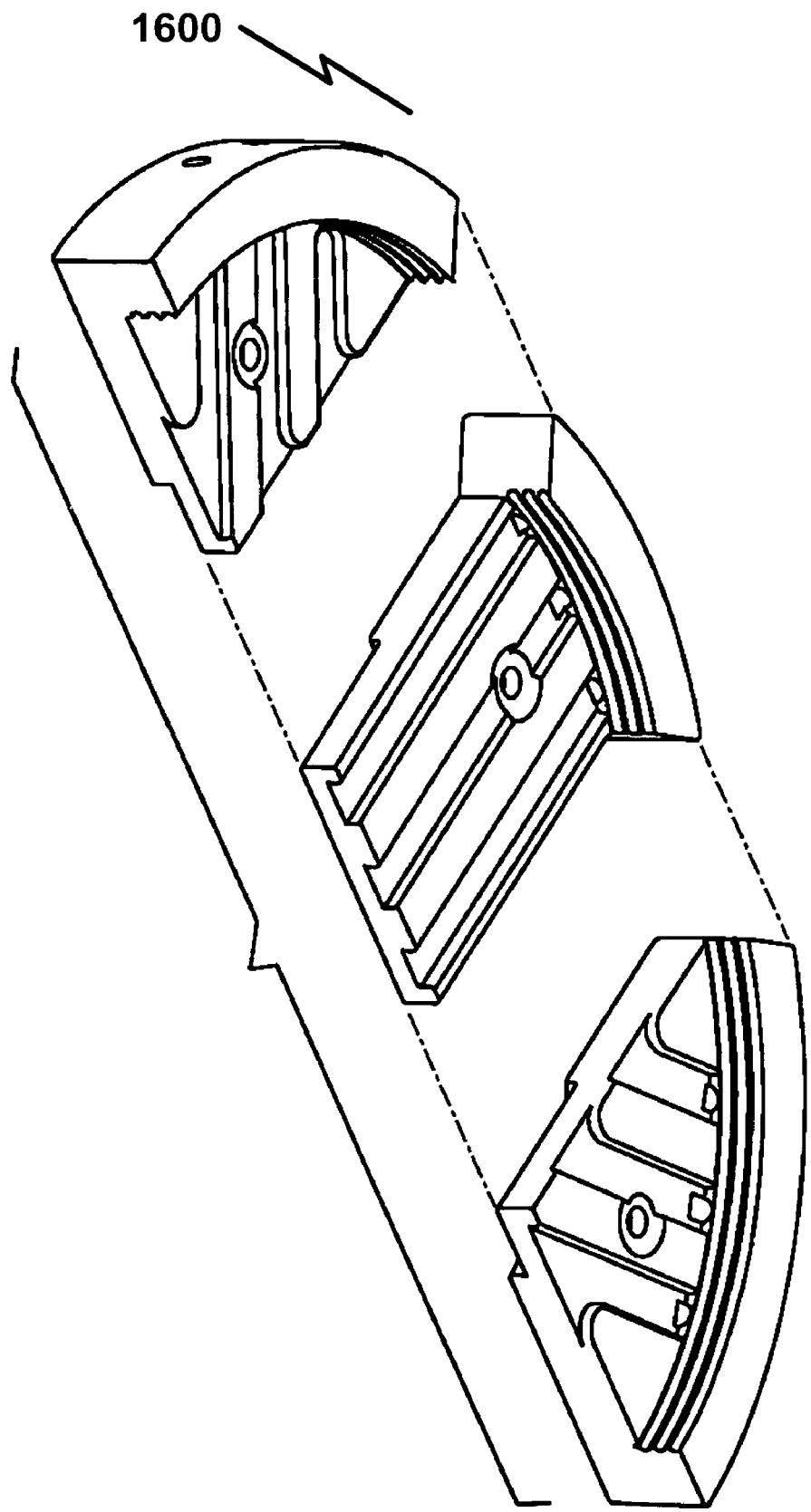
FIG. 16 illustrates a top exploded perspective view of a preferred exemplary embodiment of the upper bracket used in some embodiments of the present invention.
Figure 17:
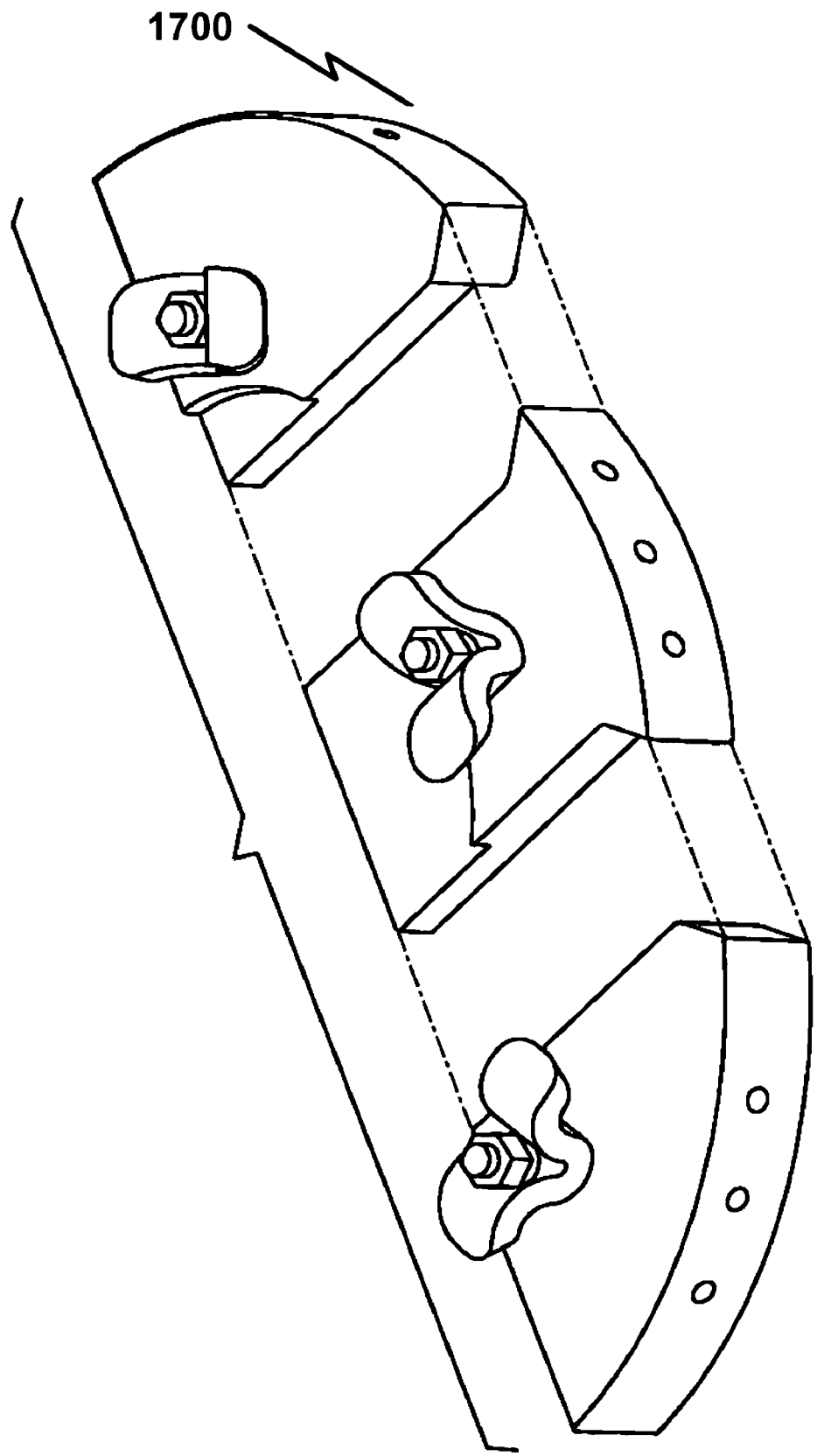
FIG. 17 illustrates a bottom exploded perspective view of a preferred exemplary embodiment of the upper bracket used in some embodiments of the present invention, showing the lateral view of the upper bracket of the spinal implant including the vertebral contact surface, cylindrical threaded projection, nut, spring and the insertion holes for adhesive.
Figure 18:
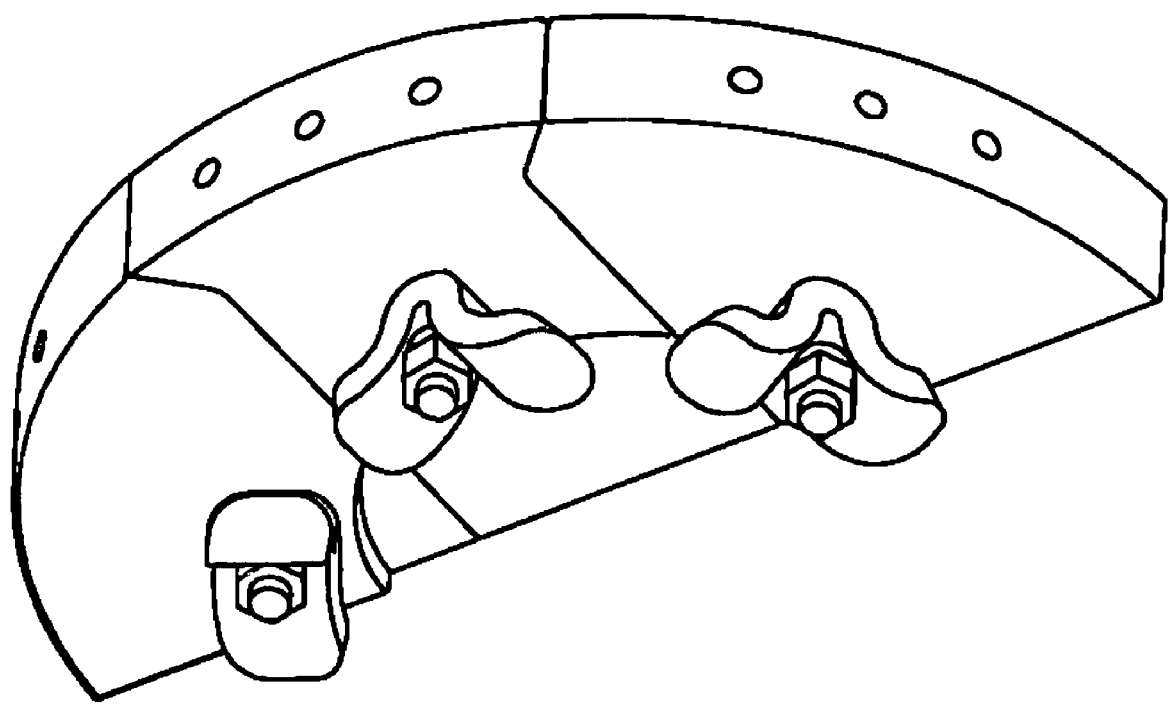
FIG. 18 illustrates a bottom perspective view of a preferred exemplary embodiment of the upper bracket used in some embodiments of the present invention.

FIG. 16 (1600), FIG. 17 (1700), and FIG. 18 (1800) illustrate exploded views of an exemplary preferred embodiment of the present invention upper bracket. FIG. 16 (1600) is a top perspective exploded view of an exemplary upper bracket, illustrating the sectional nature of the upper bracket in some preferred embodiments of the invention. As mentioned elsewhere, the sectional nature of the upper/lower brackets is preferred in many circumstances, but not necessarily required in some embodiments. FIG. 17 (1700) is a bottom perspective exploded view of an exemplary upper bracket (with springs), illustrating the sectional nature of the upper bracket in some preferred embodiments of the invention. FIG. 18 (1800) is a bottom perspective assembled view of an exemplary upper bracket (with springs), illustrating the sectional nature of the upper bracket in some preferred embodiments of the invention.

Lower Bracket Assembled Views (1900, 2000)

Figure 19:
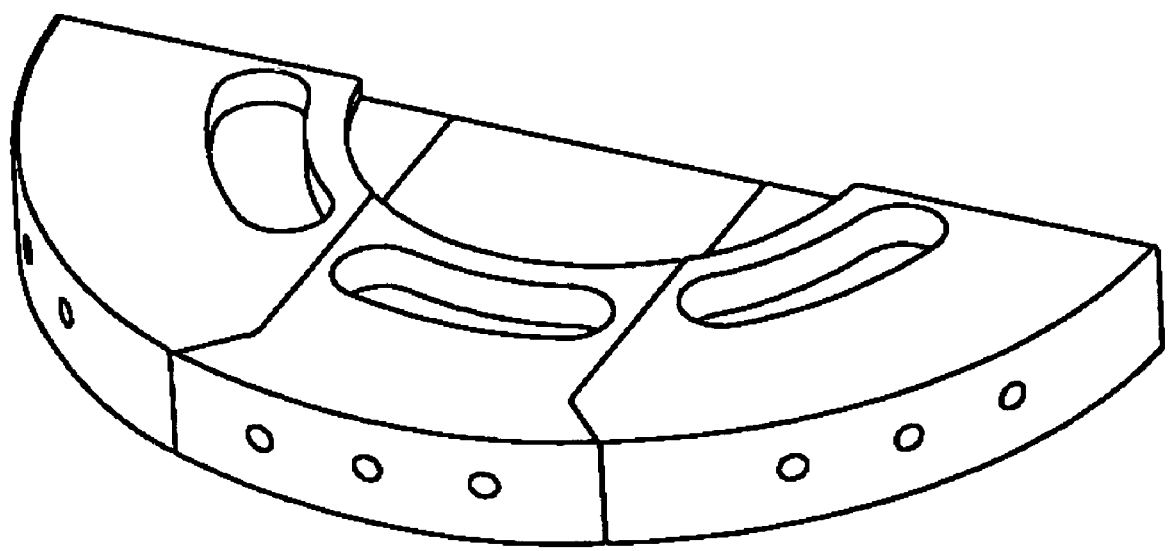
FIG. 19 illustrates a preferred exemplary embodiment of the lower bracket used in some preferred embodiments of the present invention, showing the lateral view of the lower bracket of the spinal implant including vertebral contact surface, spring guide track, inset overhang of the guide track, the insertion holes for adhesive.

FIG. 19 (1900) illustrates an assembled view of an exemplary embodiment of the bottom bracket. As mentioned elsewhere, the sectional nature of the upper/lower brackets is preferred in many circumstances, but not necessarily required in some embodiments.

As illustrated in FIG. 19 (1900), the lower bracket is the second element of the spinal implant comprising of two components, vertebral contact surface and the spring guide track. The vertebral contact surface will provide a permanent, rigid connection between the implant and the skeletal structure. The vertebral contact surface is segmented for ease of installation and providing the ability to use laparoscopic surgical insertion.

Each individual segment of the vertebral contact surface contains a spring guide track. The spring guide track is a groove that protrudes from the vertebral contact surface that contains the concave ends of an individual spring. The spring guide track is flat on the bottom and beveled on either side comprising a substantially "U" shape extending along the length of each segment of the vertebral contact surface. At either end of the segmented vertebral contact surface, there will be an inset overhang that will function as an arresting force to over-rotation. When implanted, the articulation of the spring with the spring guide track will resist axial compression between vertebrae as well as preventing lateral translation of the implant and inhibiting 360 degree motion at the vertebral level to allow normal support to the axis between the upper and lower vertebrae at the level of the spinal implant. The spring guide track (slide guards) can be altered in length to accommodate individuals with limited ROM at vertebral levels above and below the spinal implant use.

The lower bracket vertebral contact surface is otherwise the same as the upper bracket vertebral contact surface. Located at the midpoint but on the lateral surface are insertion holes on each segment. The three segments of the vertebral contact surface component of the lower bracket are meant to configure together to comprise the single unit of the lower bracket. The bracket will extend from the outer edge of the skeletal structure to the interior, inferior surface of the vertebral body, but generally not to exceed the diameter of the vertebral body. Either end of the vertebral contact surface will be angled toward the skeletal structure so that the surfaces are flush, making a cavity that the adhesive can fill in to. The under surface of the bracket that contacts the skeletal surface can be textured/hatched to allow for maximum surface area to improve adhesion of the implant to the bone. The adhesive will be injected through the insertion holes on the lateral surface of each segment.

Alternatively, the spring and spring guide track component could be replaced with a series of collapsible cylinders, akin to shock absorbers. A spiral spring could be substituted for the concave/convex spring configuration. The spring could be made as a permanent part of the top bracket and eliminate the bolt and threaded cylinder attachment. The vertebral contact surface could be all one piece instead of a three-segmented jigsaw. The U-shape of the bottom bracket spring guide could be a flat half circle. The adhesive choice for attachment of the upper and lower bracket could be substituted for teeth or other type of sharp protuberance that could be affixed to the vertebrae. The adhesive choice could be substituted with screws used to secure the upper and lower brackets to the skeletal structure from the lateral, overlapping portion of the vertebral contact surface. The spring and spring guide track component could be replaced with a collapsible honeycomb structure made of biocompatible material not yet determined, and that would be secured by other means.

Figure 20:
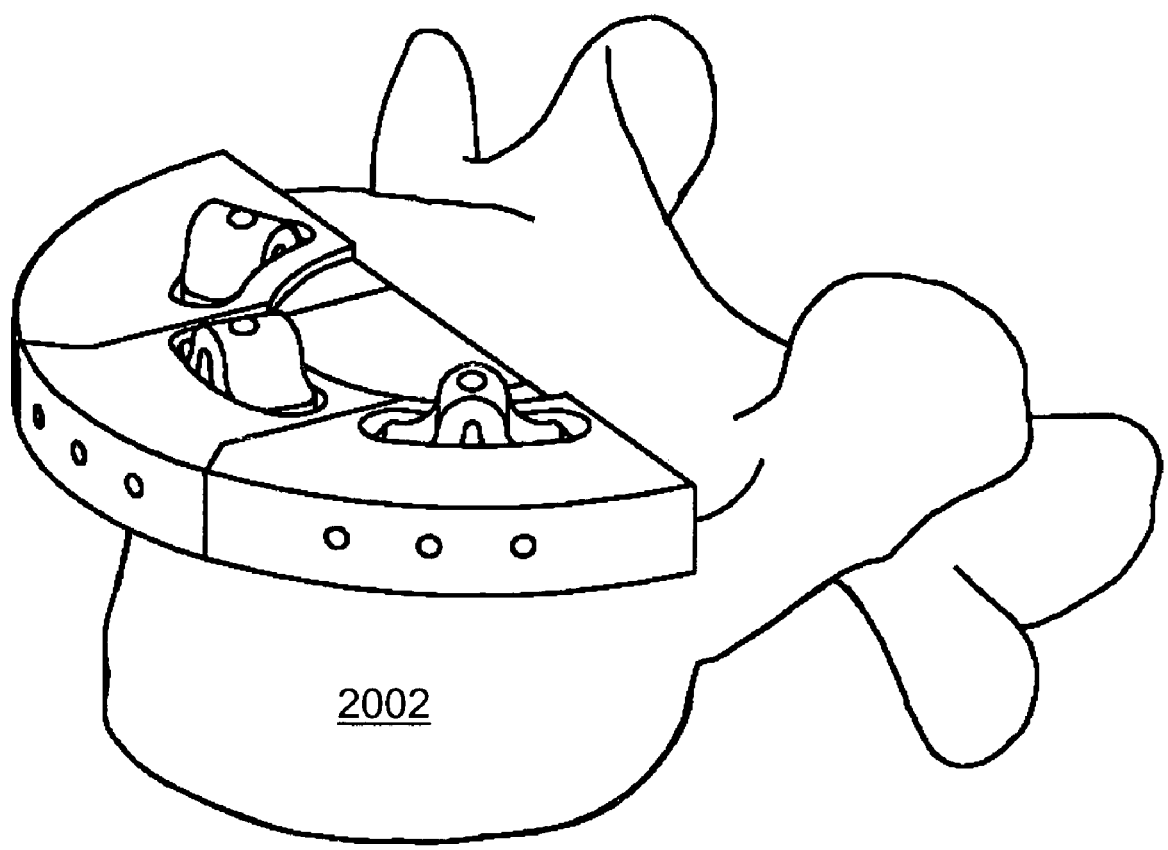
FIG. 20 illustrates the lateral view of the spring guide track in the lower bracket vertebral contact surface with springs from the upper bracket assembly properly positioned.

FIG. 20 (2000) illustrates an exemplary embodiment of the bottom bracket as installed on a lower spinal vertebrae (2002) and illustrates how the springs (which are attached to the upper bracket that is not depicted in this illustration) rest in the spring guide tracks on the lower bracket. This spring/ guide track configuration provides full ROM for the patient as well as providing shock absorption for the spinal column.

Upper/Lower Bracket Detail (2100, 2200, 2300, 2400)

Figure 21:
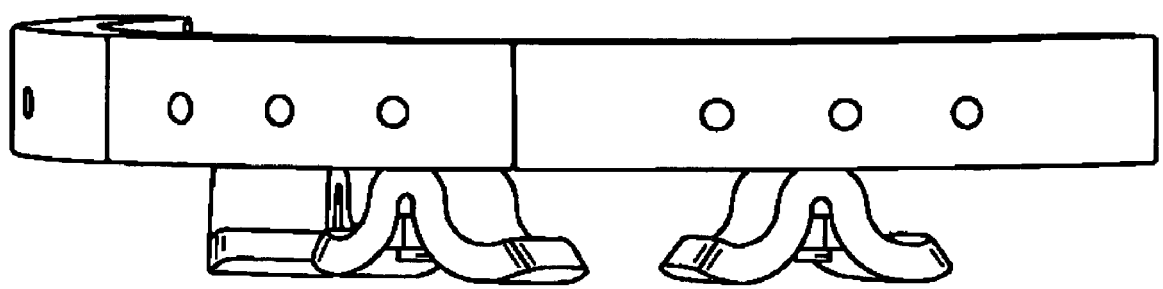
FIG. 21 illustrates a side view of a preferred exemplary embodiment of the upper bracket of the present invention.
Figure 22:
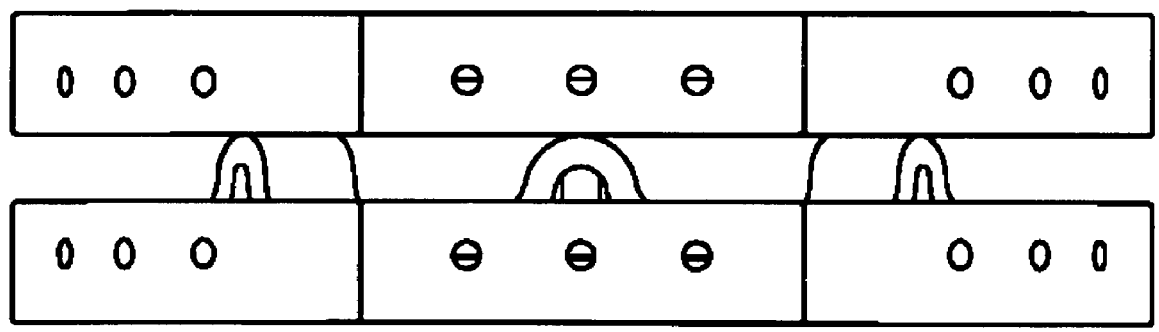
FIG. 22 illustrates a front view of a preferred exemplary embodiment of the top and bottom bracket assemblies and springs of the present invention.
Figure 23:
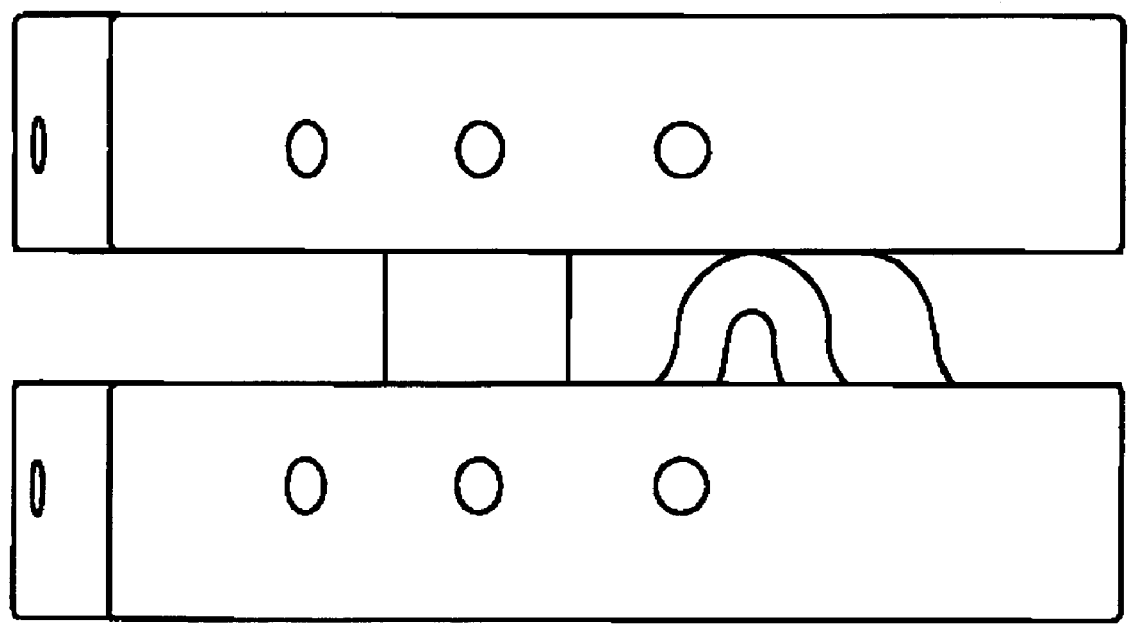
FIG. 23 illustrates a side view of a preferred exemplary embodiment of the top and bottom bracket assemblies and springs of the present invention.
Figure 24:
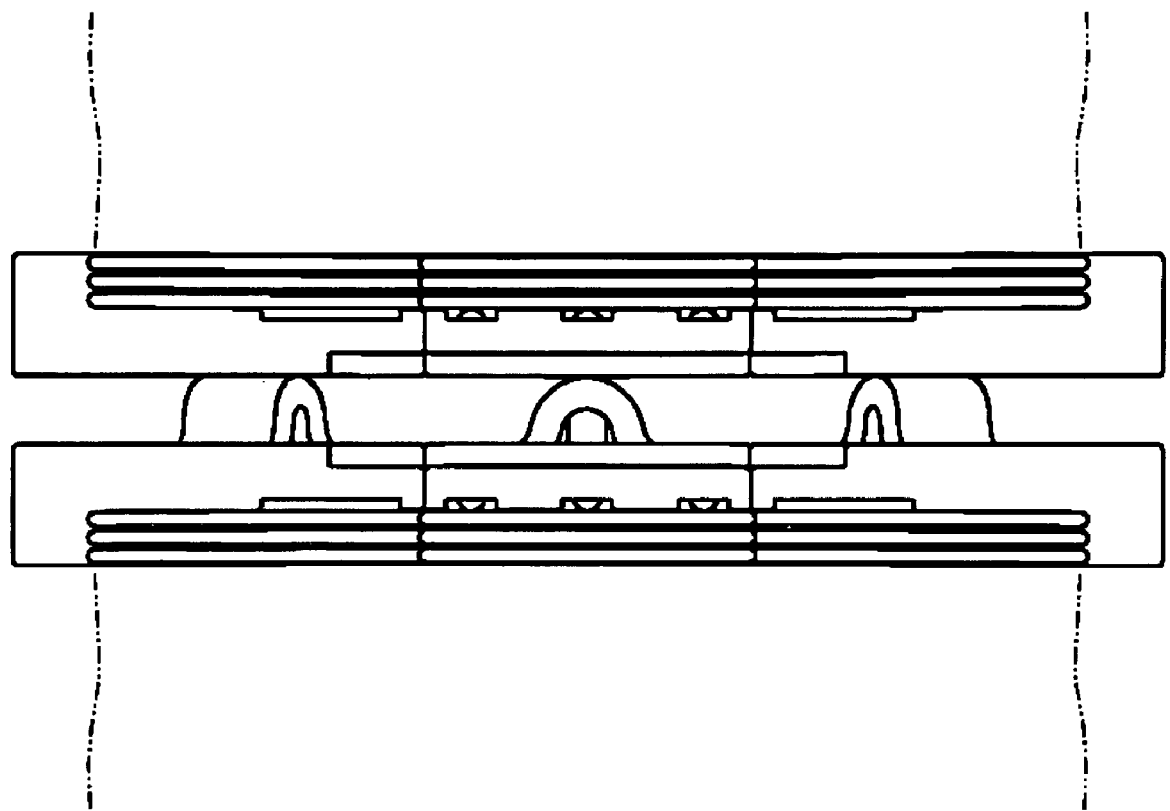
FIG. 24 illustrates a back sectional view of a preferred exemplary embodiment of the top and bottom bracket assemblies of the present invention as applied to a typical spinal upper and lower vertebrae.

While the upper and lower brackets generally illustrated in FIG. 8 (0800) can take many forms, detailed illustrations of a preferred embodiment of these components is illustrated in FIG. 21 (2100), FIG. 22 (2200), FIG. 23 (2300), and FIG. 24 (2400).

As depicted in FIG. 20 (2000) and FIG. 21 (2100), the spring component of the upper bracket element of the spinal implant will permit pivotal movement between the vertebrae and is the key component to the restoration of ROM in the spinal section. The term pivotal is intended to describe either or both of a rotation or twisting motion about the support axis and/or a tilting motion angularly inclined in any direction relative to the support axis.

The spring has a general configuration of an alternating concave and convex shape. As generally illustrated in FIG. 20 (2000), some preferred invention embodiments will comprise a convex portion of the spring having a hole to fit into the cylindrical projection of the upper bracket. The two remaining concave portions will fit into the tracks of the lower bracket as illustrated in FIG. 20.

As illustrated in FIG. 8 (0800), the nut (0822) component of the upper bracket element of the spinal implant will attach the spring to the upper bracket. The nut is preferably, but not limited to, hexagonal in shape with a rounded surface contacting the spring component. The nut can only be inserted, therefore, in one direction, so that the rounded end threads onto the cylindrical threaded projection of the upper bracket in the direction that it contacts the spring component first. The rounded end of the nut may in many preferred embodiments correspond with the convex angle of the spring that it is attaching to the upper bracket. The nut is preferably fabricated from or coated with materials on threads to aid in fixation (self-locking) such as a low-friction, wear- and impact-resistant, biocompatible material such as (for example) polyethylene, non-absorbable polymers or other biocompatible polymeric.

FIG. 22 (2200) illustrates a side view (from the patient's front perspective) of an exemplary embodiment of the present invention and generally illustrates the adhesive injection holes/ports, three piece preferred sectional design, and tri-spring interface between the upper and lower brackets.

FIG. 23 (2300) illustrates a side view (from the patient's side perspective) of an exemplary embodiment of the present invention and generally illustrates the adhesive injection holes/ports, preferred sectional design, and multi-spring interface between the upper and lower brackets.

FIG. 24 (2400) illustrates a frontal sectional assembled view (from the patient's back perspective) of an exemplary embodiment of the present invention as installed between upper and lower spinal vertebrae and generally illustrates the spring guide tracks, preferred sectional design, and multi-spring interface between the upper and lower brackets.

Fastening Variation

Inverted Acorn Nuts (2500, 2600)

Figure 25:
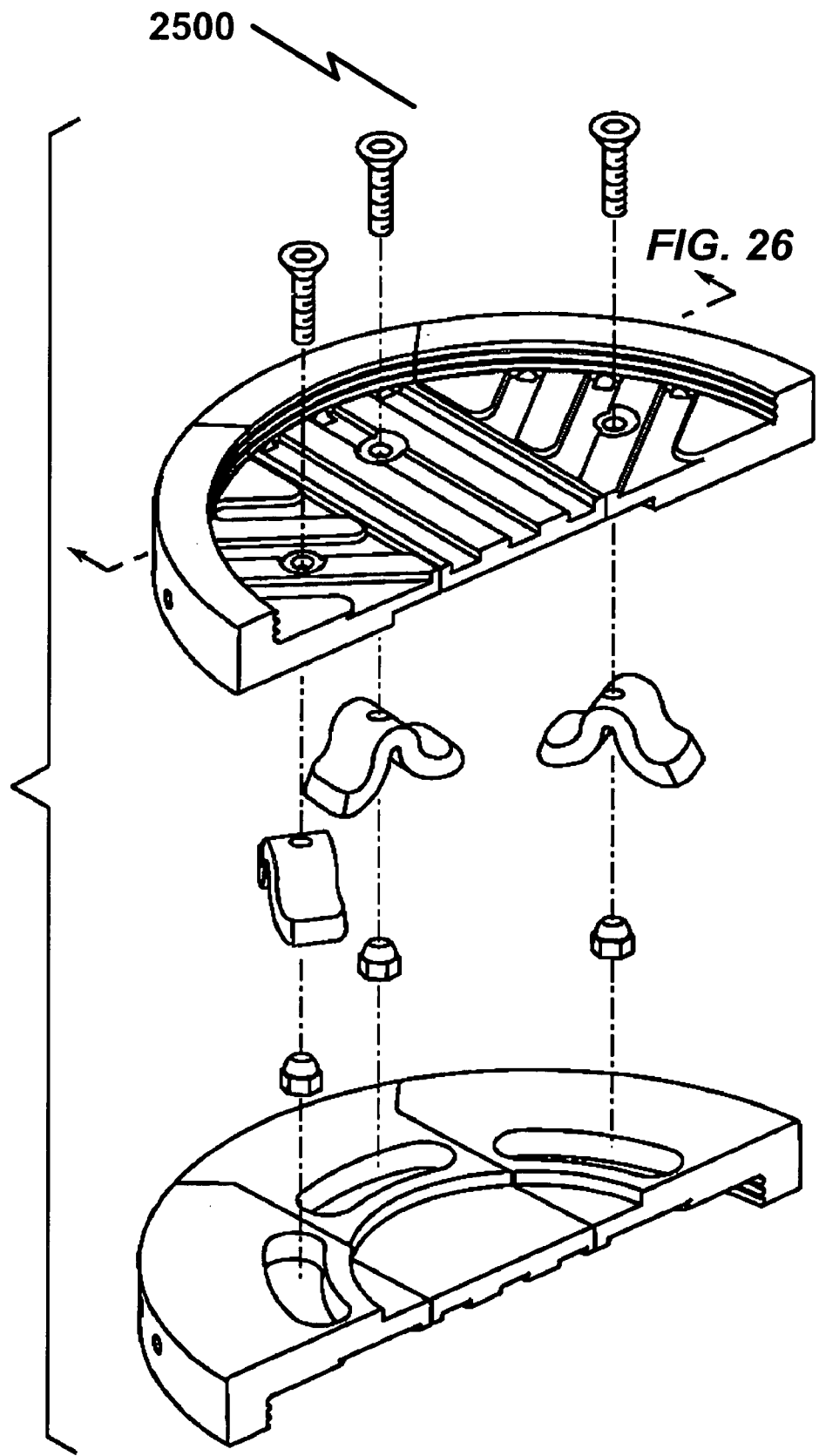
FIG. 25 illustrates an exploded view of a preferred exemplary embodiment of the present invention using screw/nut fasteners for the springs.
Figure 26:
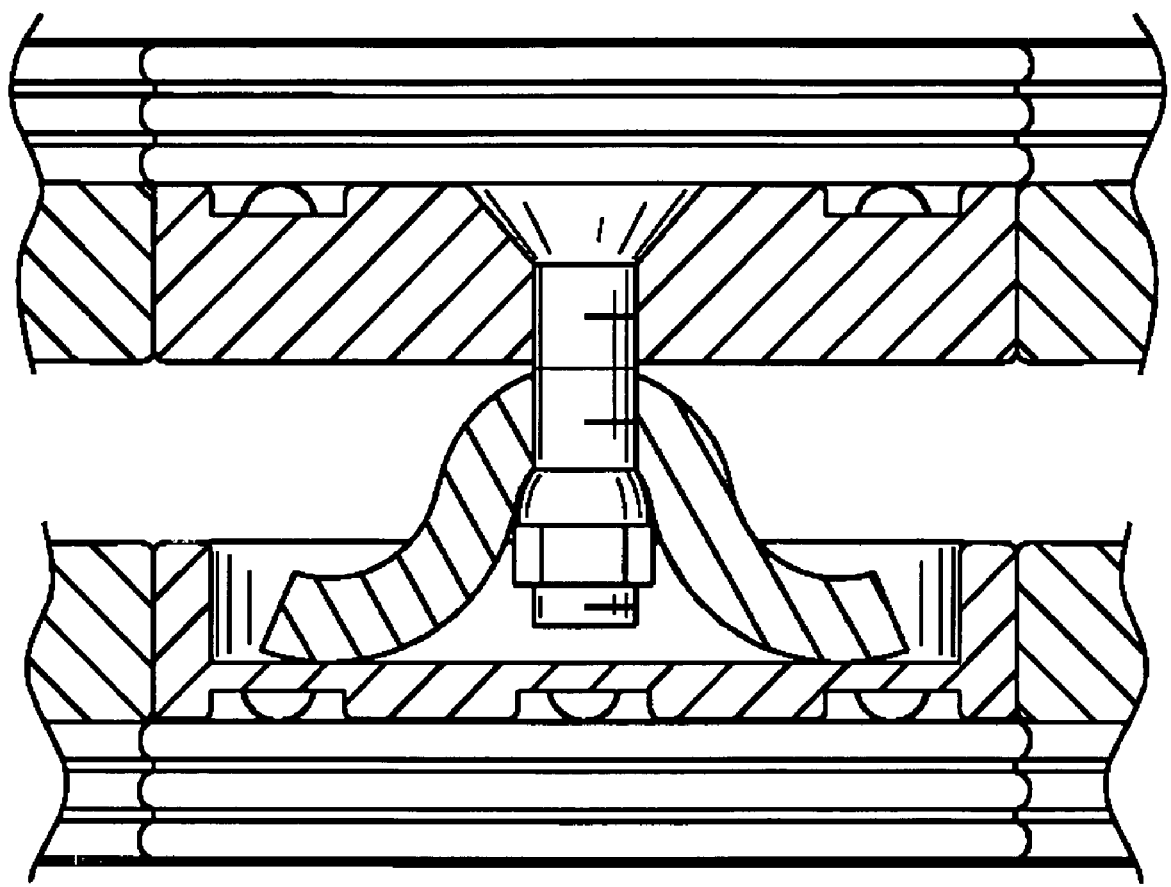
FIG. 26 illustrates a side sectional view of the preferred exemplary embodiment illustrated in FIG. 25.

While a wide variety of methods are available for fastening springs to the upper bracket, one preferred embodiment is illustrated in exploded view FIG. 25 (2500) and associated sectional side view FIG. 26 (2600) wherein inverted acorn nuts and inset cap screws are used as fasteners to attach the springs to the upper bracket.

Fastening Variation

Spring Captors (2700, 2800)

Figure 27:
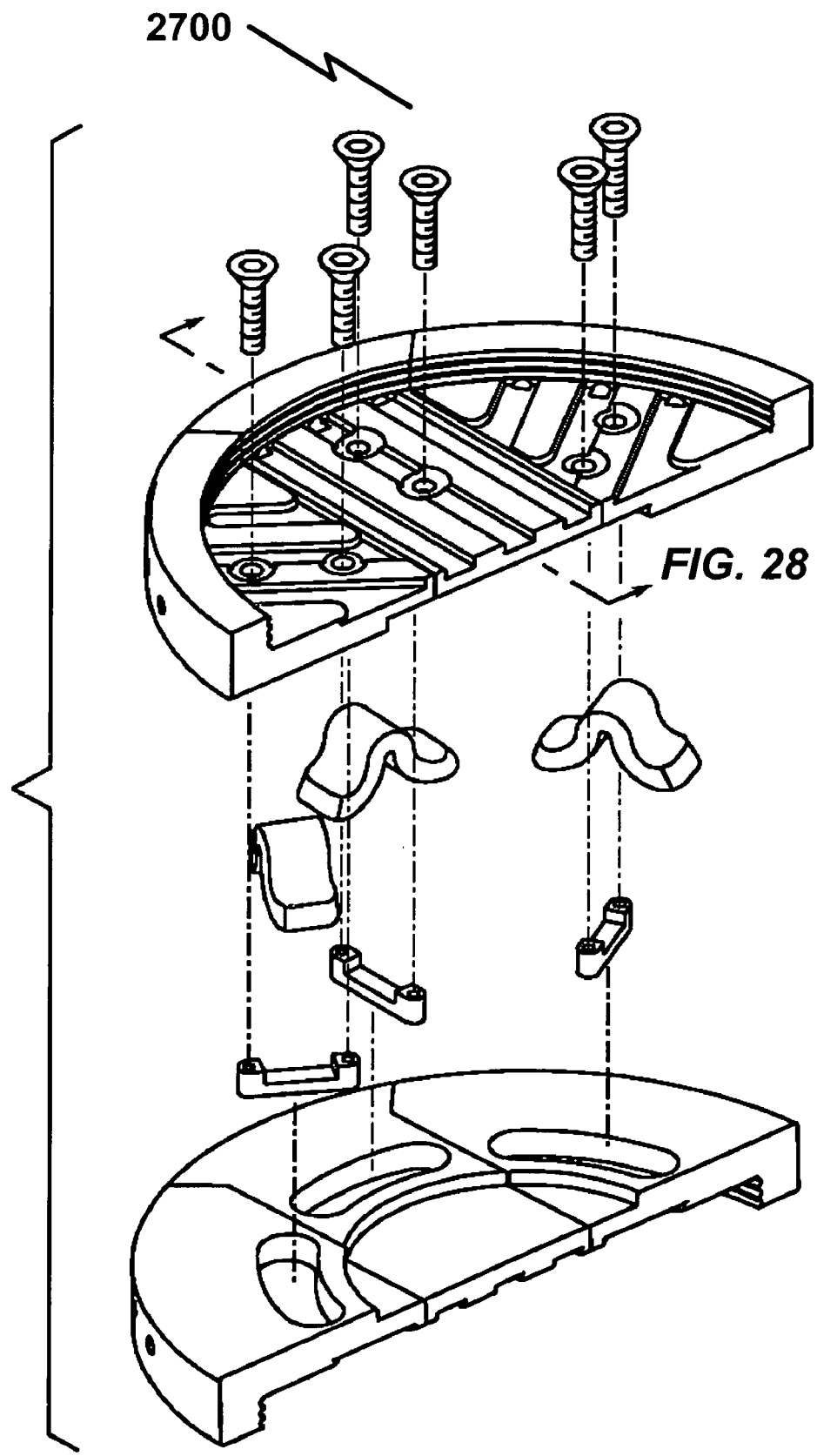
FIG. 27 illustrates an exploded view of a preferred exemplary embodiment of the present invention using screw/"U" bracket fasteners as an alternative spring fastening means.
Figure 28:
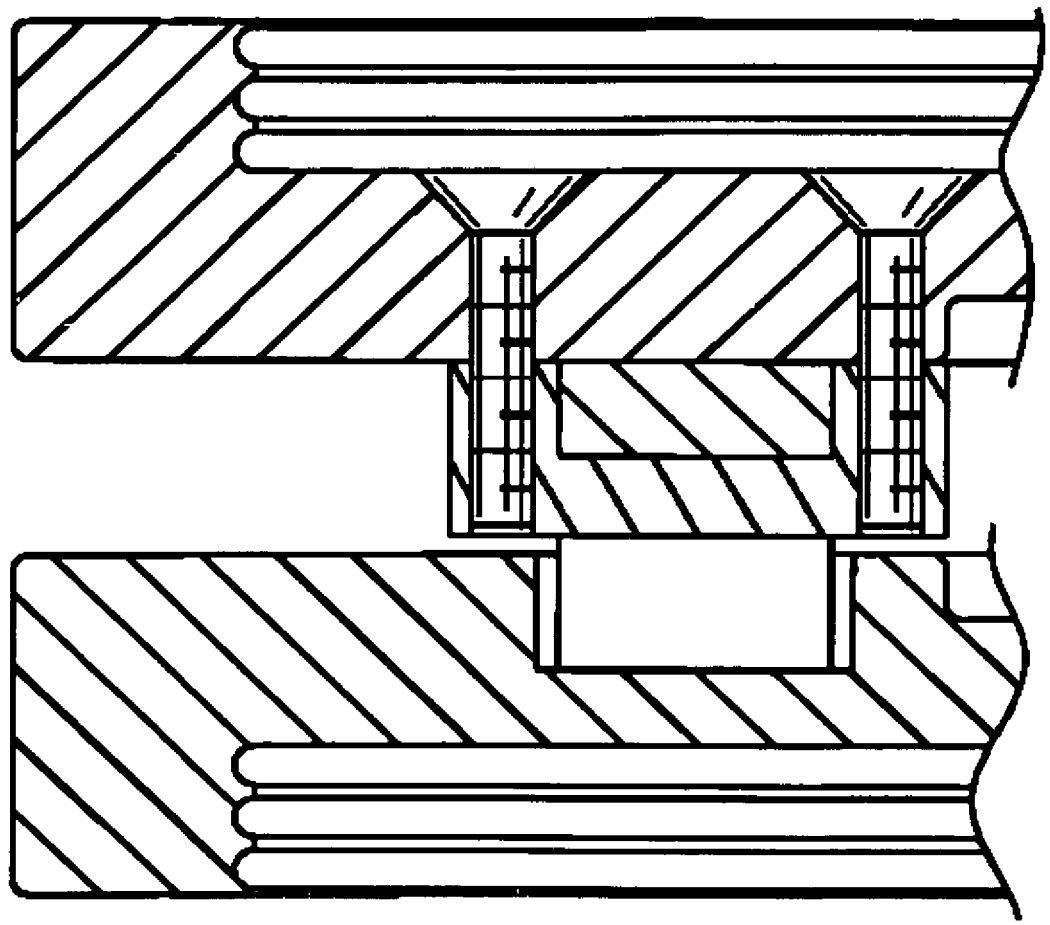
FIG. 28 illustrates a side sectional view of the preferred exemplary embodiment illustrated in FIG. 27.

While a wide variety of methods are available for fastening springs to the upper bracket, another preferred embodiment is illustrated in exploded view FIG. 27 (2700) and associated sectional side view FIG. 28 (2800) wherein U-shaped spring brackets (U-bolt) are used as a retaining means to attach the springs to the upper bracket.

The cylindrical projection may be enhanced in the form of a U-bolt to replace the upper bracket's cylindrical projection (pseudo screw). The configuration of the U-bolt is exactly as implied by the term "U". The cylindrical projection would be lengthened sufficiently to allow the material to be formed into a "U" configuration, as shown in FIG. 27 (2700).

Both ends of the "U" would be secured to the upper bracket. The ends of the "U" could be deformed as described in the rivet enhancement, or threaded to accept a low profile nut.

Installation of this type of spring fastener is as follows. A spring would be placed between the vertical legs of the "U" bolt. The ends of the "U" would be inserted into respective drilled holes in the upper bracket sections. The ends would then be secured to the upper bracket using a mechanical process, (e.g. rivet operation, low profile nut, etc.)

Fastening Variation

Rivets (2900, 3000)

Figure 29:
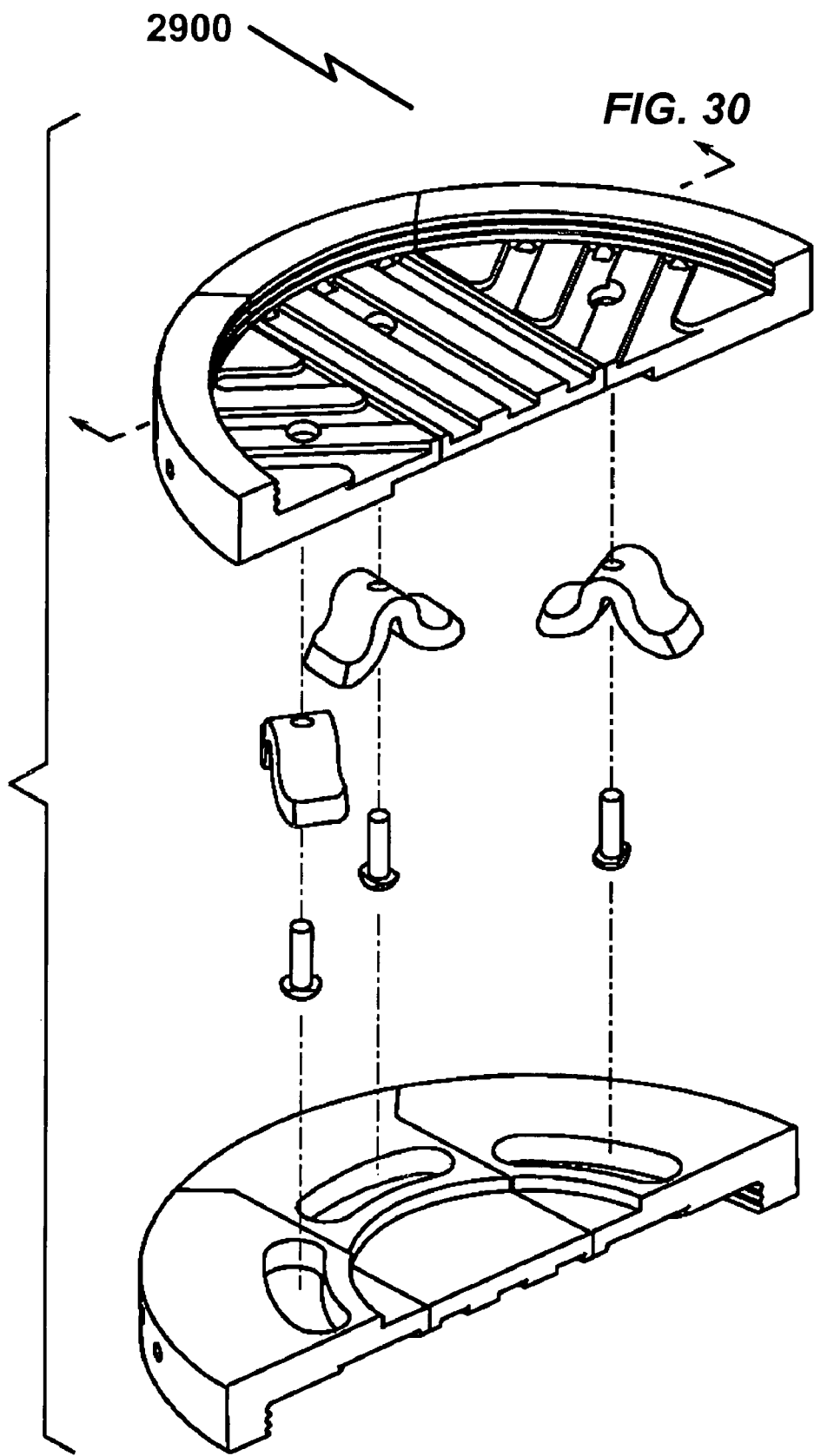
FIG. 29 illustrates an exploded view of a preferred exemplary embodiment of the present invention using rivet fasteners for the springs.
Figure 30:
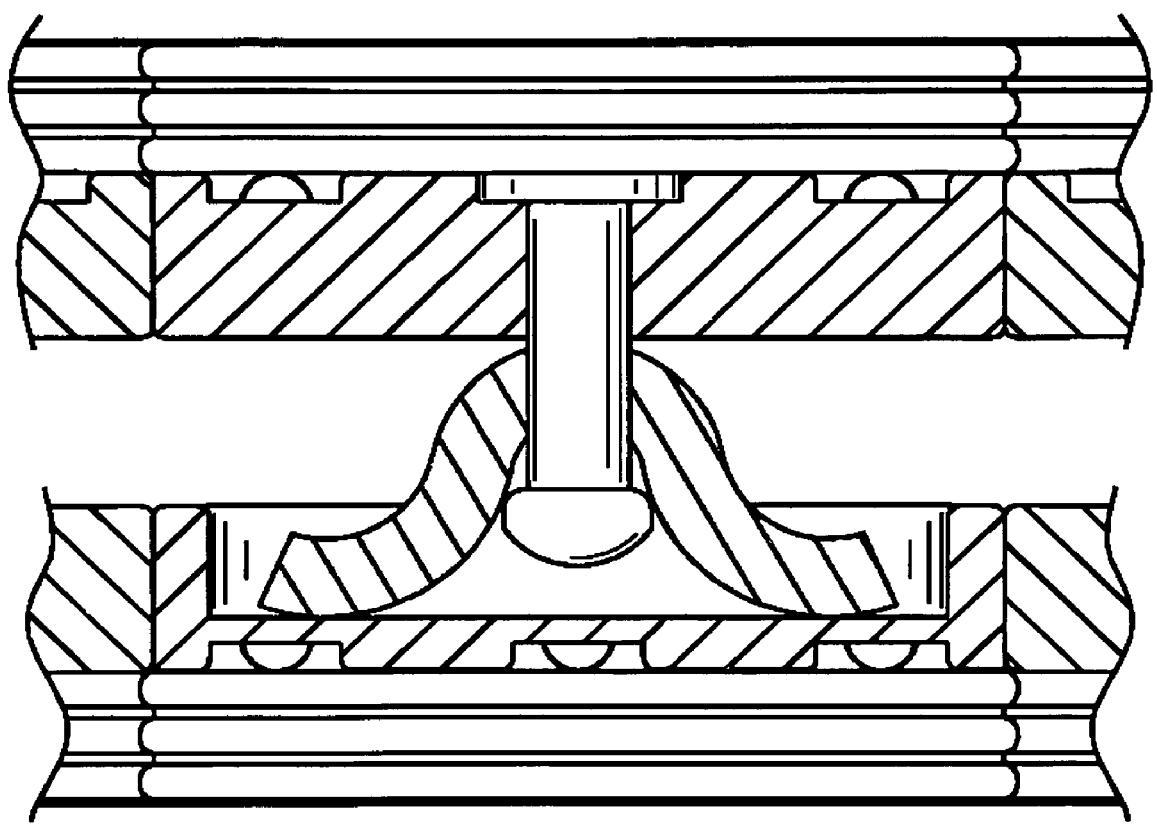
FIG. 30 illustrates a side sectional view of the preferred exemplary embodiment illustrated in FIG. 29.

While a wide variety of methods are available for fastening springs to the upper bracket, another preferred embodiment is illustrated in exploded view FIG. 29 (2900) and associated sectional side view FIG. 30 (3000) wherein rivets are used as fasteners to attach the springs to the upper bracket.

The cylindrical projection described previously can be enhanced by replacement of the cylindrical projection with a rivet enhancement. The rivet is a cylindrical piece of surgical compatible material capable of being intentionally deformed to secure the spring to the upper bracket The rivet may contain a cylindrical diameter over which a spring could be placed. One end of the rivet cylindrical diameter would then be placed in a drilled hole in the upper bracket. The location of this drilled hole would be the same location as the existing cylindrical projection described previously.

The cylindrical diameter ends of the rivet material would be secured in a clamping device. This clamping device would exert sufficient compressive force on the rivet material to cause the material to deform to the curved portion of the spring and the flat upper bracket surfaces. The amount of clamping force and resulting deformation of the rivet material would be controlled to allow the spring to function as previously described.

Fastening Variation

Acorn Nuts (3100, 3200)

Figure 31:
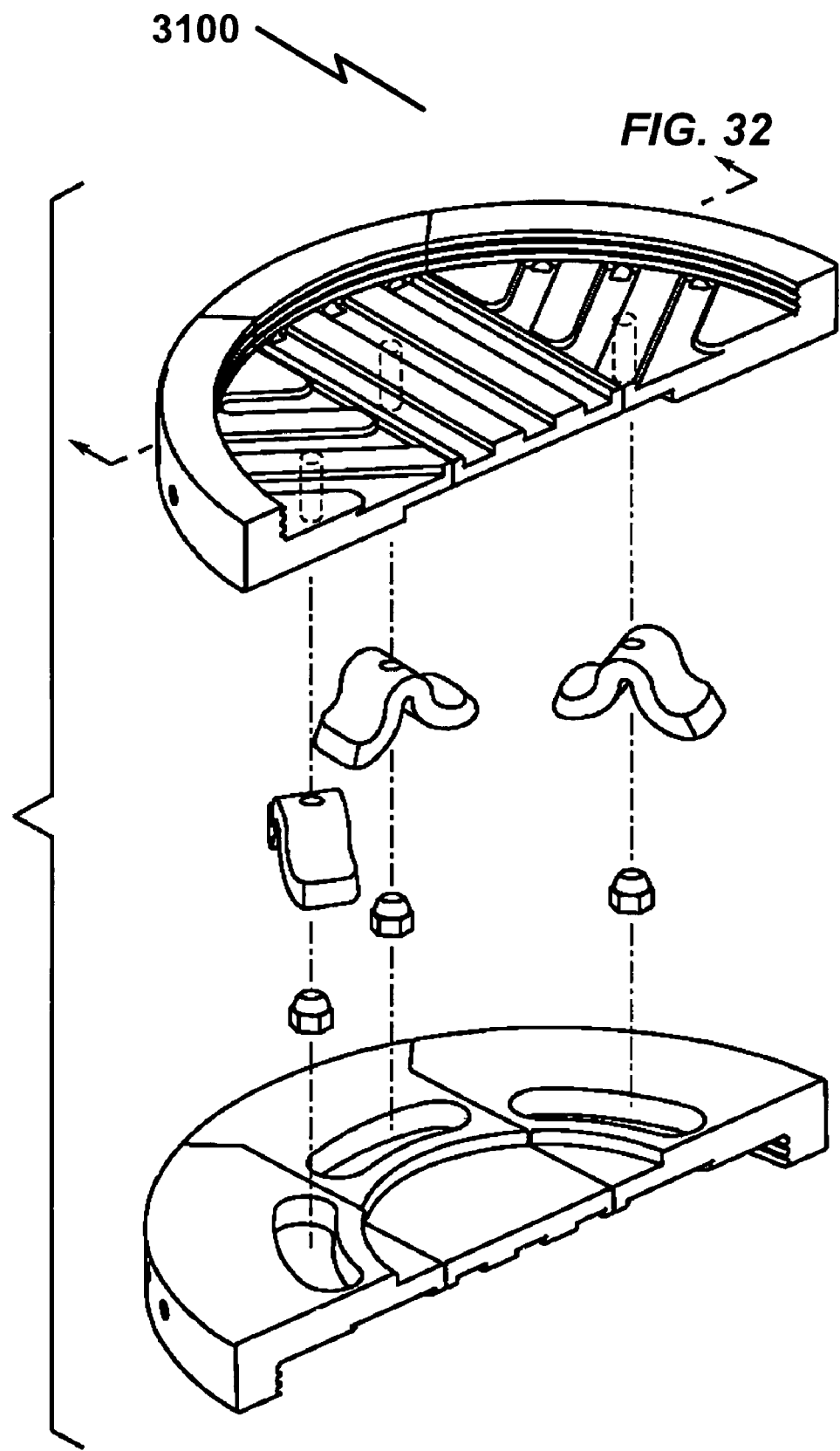
FIG. 31 illustrates an exploded view of a preferred exemplary embodiment of the present invention using threaded projections common to the upper bracket and nut fasteners for the springs.
Figure 32:
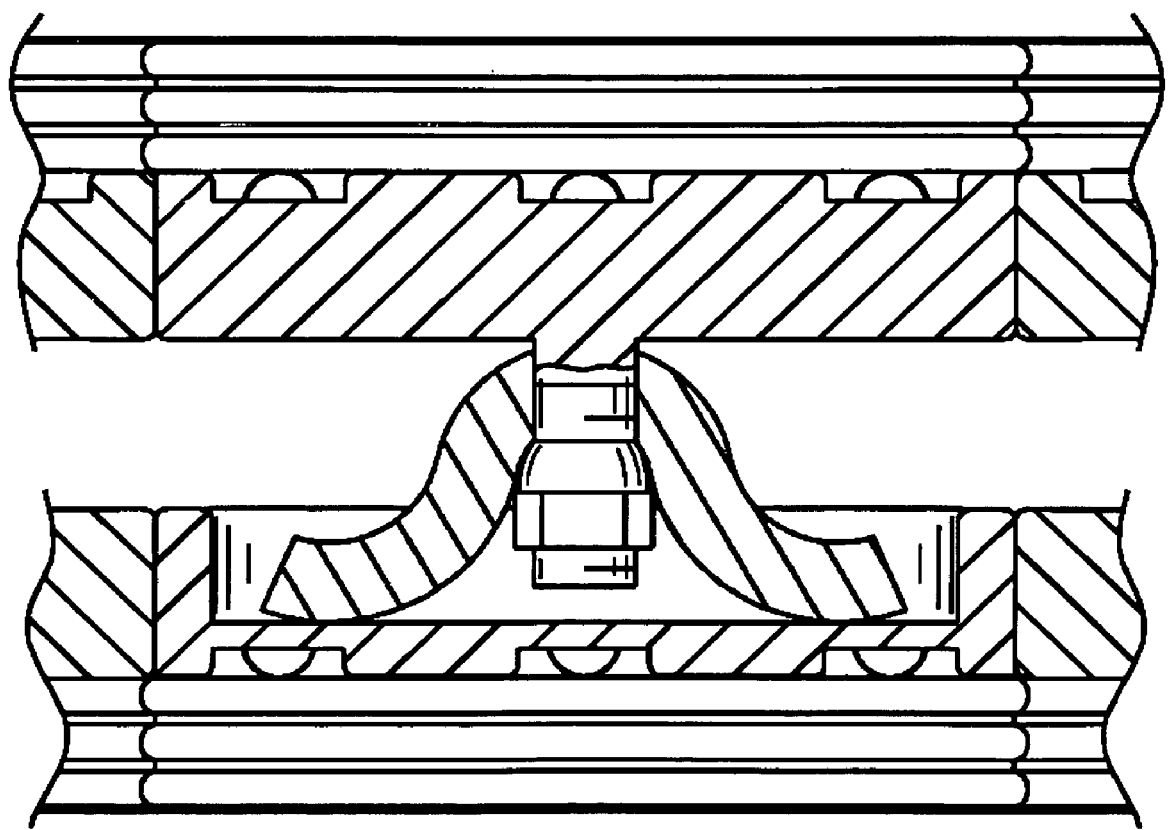
FIG. 32 illustrates a side sectional view of the preferred exemplary embodiment illustrated in FIG. 31.

While a wide variety of methods are available for fastening springs to the upper bracket, one preferred embodiment is illustrated in exploded view FIG. 31 (3100) and associated sectional side view FIG. 32 (3200) wherein enclosed acorn nuts and inset cap screws are used as fasteners to attach the springs to the upper bracket.

Non-Co-Planar Disc Structure (3300, 3400)

The present invention may be implemented using co-planar upper/lower brackets as illustrated herein in some embodiments. However, the invention may incorporate non-co-planar (non-planar) disc structures in which the upper and/or lower bracket is tapered rather than co-planar, permitting the replacement disc structure to more fully conform to the requirements of the replaced disc in the patient.

Figures 33, 34:
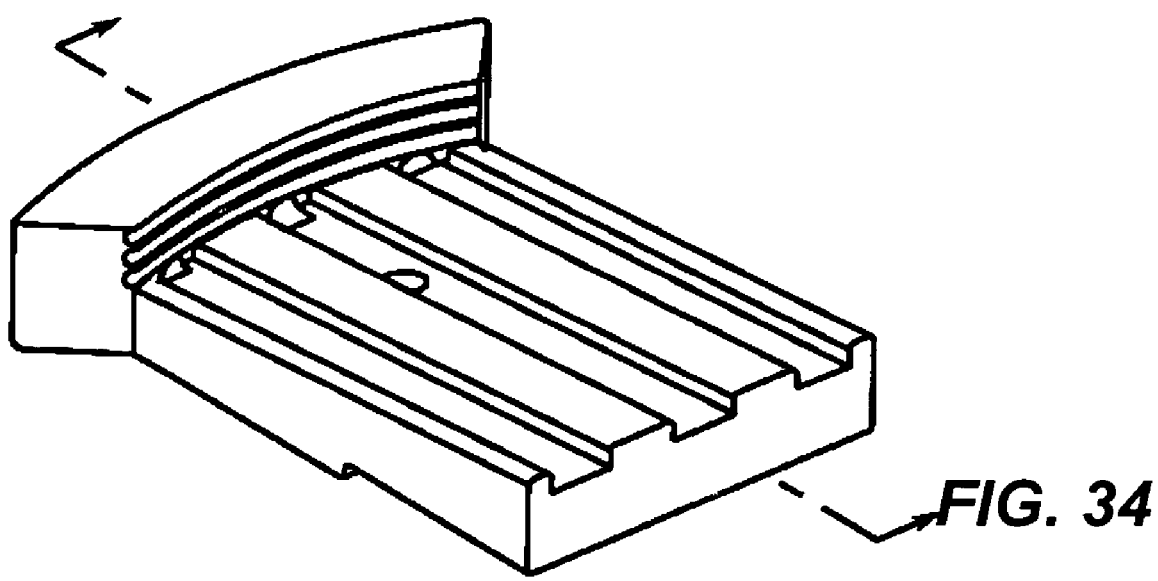
FIG. 33 illustrates a preferred exemplary embodiment of the present invention wherein the lower bracket is non-coplanar.
FIG. 34 illustrates a side sectional view of the preferred exemplary embodiment illustrated in FIG. 33.
Figure 34:
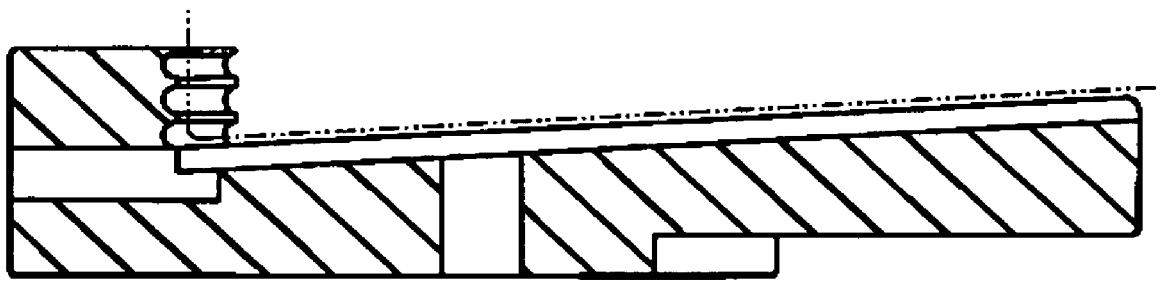

This alternate embodiment illustrating non-co-planar structure is depicted in FIG. 33 (3300) with side sectional view illustrated in FIG. 34 (3400) more fully illustrating the tapered nature of the bracket construction. The views in FIG. 33 and FIG. 34 only illustrate one bracket as an example of non-planar (non-co-planar) structures. Note that the present invention anticipates any combination of co-planar and non-planar upper and/or lower brackets.

Vertebral Contact Surface Conditioning (3500, 3600, 3700, 3800)

The present invention anticipates that the contact surface between the upper bracket (upper vertebral contact surface) and the upper spinal vertebrae and/or the surface between the lower bracket (lower vertebral contact surface) and the lower spinal vertebrae may be surface conditioned for improved adhesion between the artificial spinal disc replacement and the surrounding vertebrae.

This surface conditioning can take many forms, including abrasion of the contact surface, chemical treatment, mechanical polishing, machining, and/or knurling. The present invention does not limit the scope of this surface conditioning, and one skilled in the art will be able to delineate a wide variety of surface conditioning techniques appropriate in this application.

Figure 35:
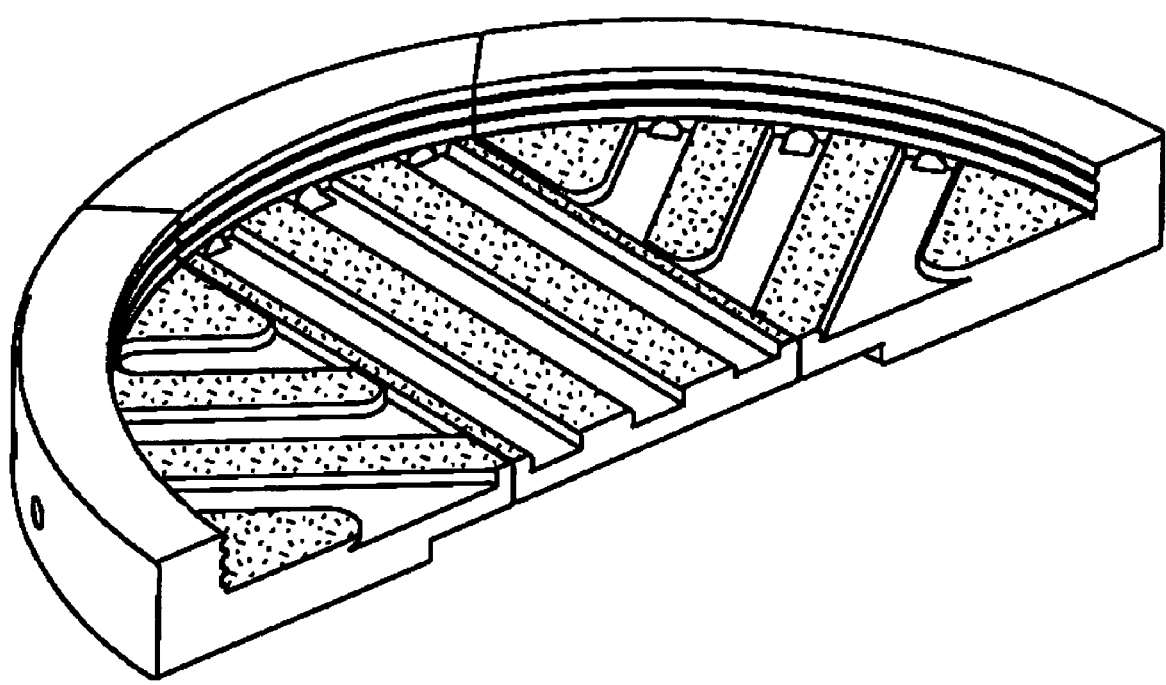
FIG. 35 illustrates a preferred exemplary embodiment of the present invention wherein the upper/lower bracket vertebral contact surface has been partially surface conditioned to promote improved adhesion to the upper spinal vertebrae.
Figure 36:
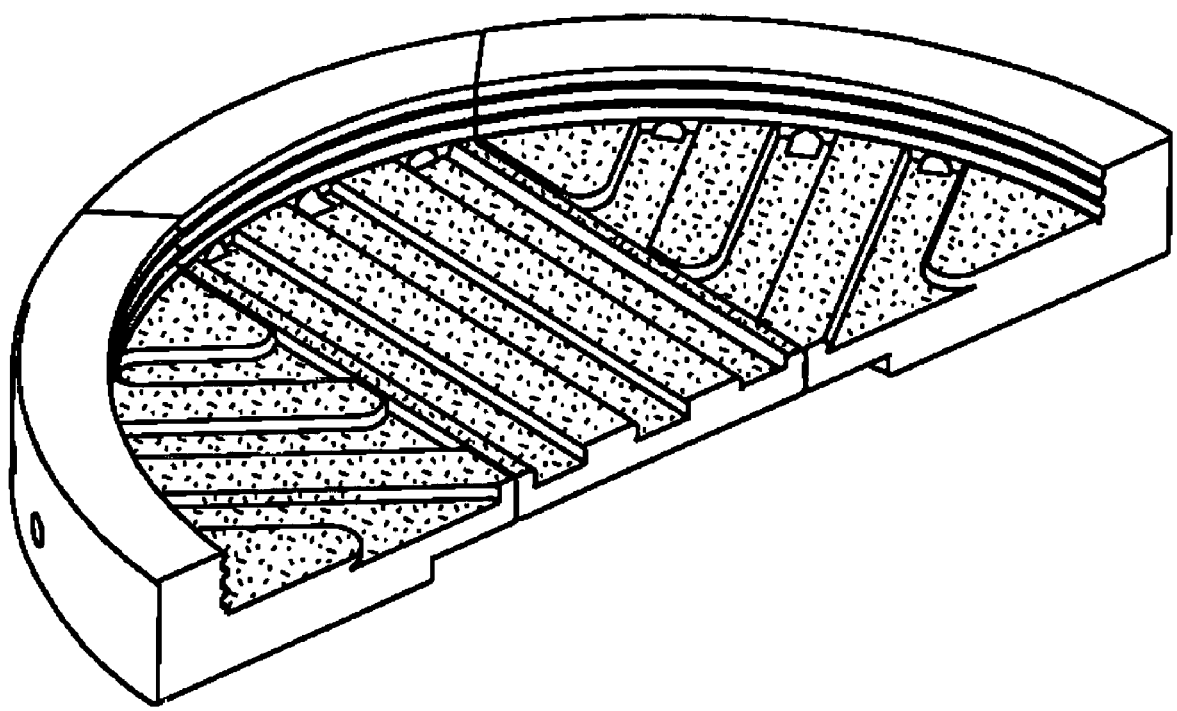
FIG. 36 illustrates a preferred exemplary embodiment of the present invention wherein the upper/lower bracket vertebral contact surface has been fully surface conditioned to promote improved adhesion to the upper spinal vertebrae.
Figure 37:
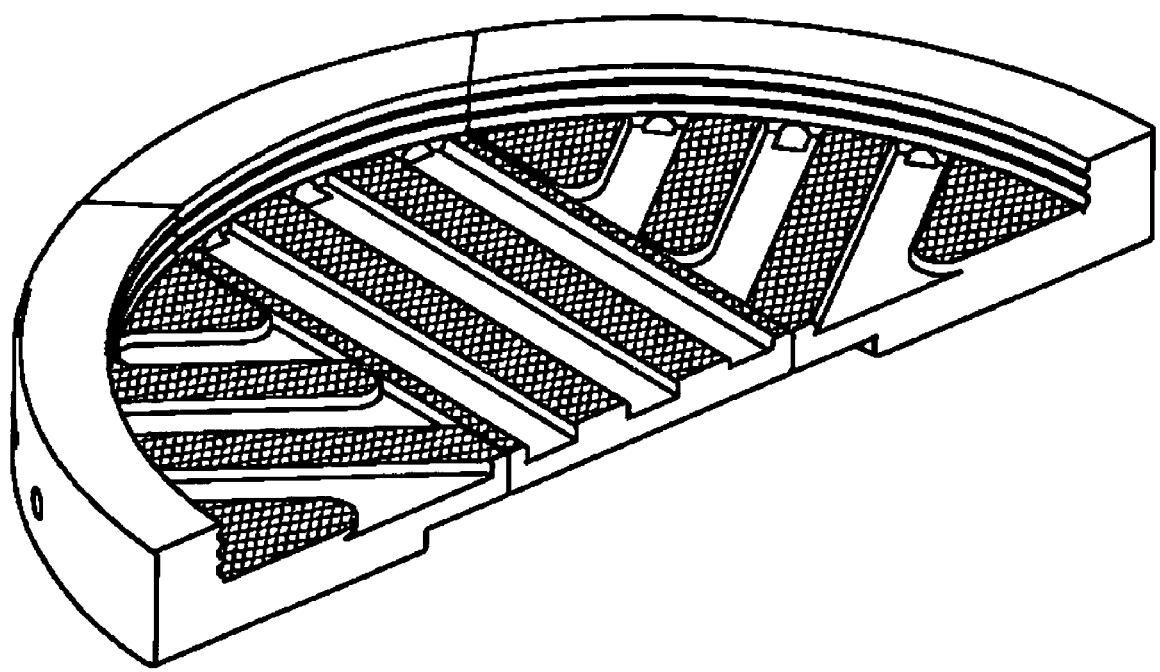
FIG. 37 illustrates a preferred exemplary embodiment of the present invention wherein the upper/lower bracket vertebral contact surface has been partially knurled to promote improved adhesion to the upper spinal vertebrae.
Figure 38:
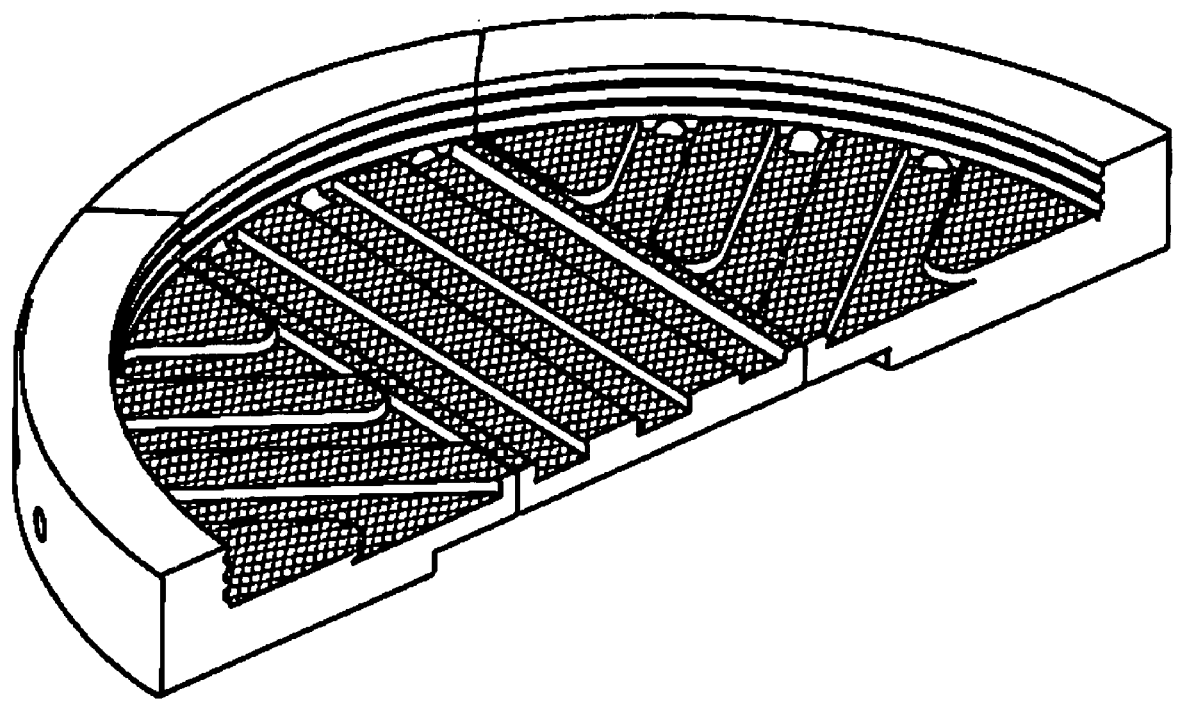
FIG. 38 illustrates a preferred exemplary embodiment of the present invention wherein the upper/lower bracket vertebral contact surface has been fully knurled to promote improved adhesion to the upper spinal vertebrae.

Examples of exemplary embodiments implementing surface conditioning are illustrated in FIG. 35 (3500), FIG. 36 (3600), FIG. 37 (3700), and FIG. 38 (3800). Note, as contrasted in FIG. 35 (3500) and FIG. 36 (3600) as well as FIG. 37 (3700) and FIG. 38 (3800) that the surface conditioning may be either partial (3500, 3700) and/or total (3600, 3800). One skilled in the art will recognize that more than one type of surface conditioning may be performed on the upper/lower brackets in some circumstances with no loss of generality in the scope of the present invention.

Alternative Spring Structures (3900)

Figure 39:
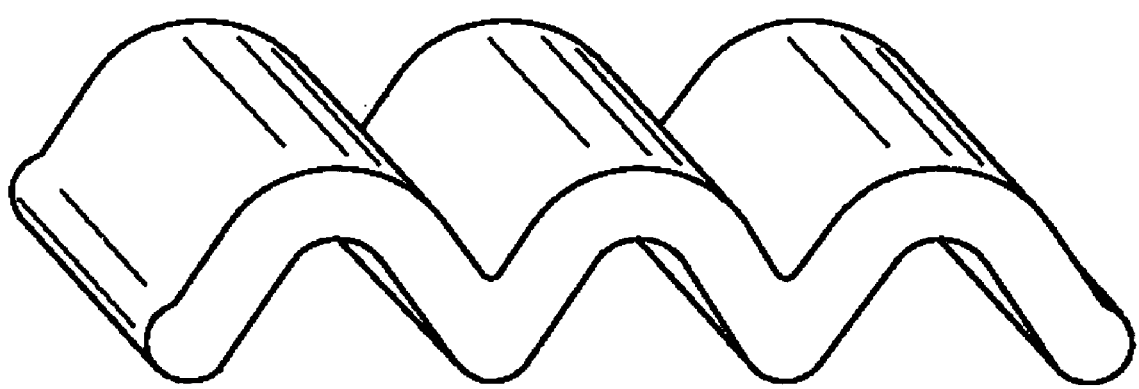
FIG. 39 illustrates an alternative preferred exemplary embodiment of a spring structure suitable for use in some preferred exemplary embodiments of the present invention.
Figure 40:
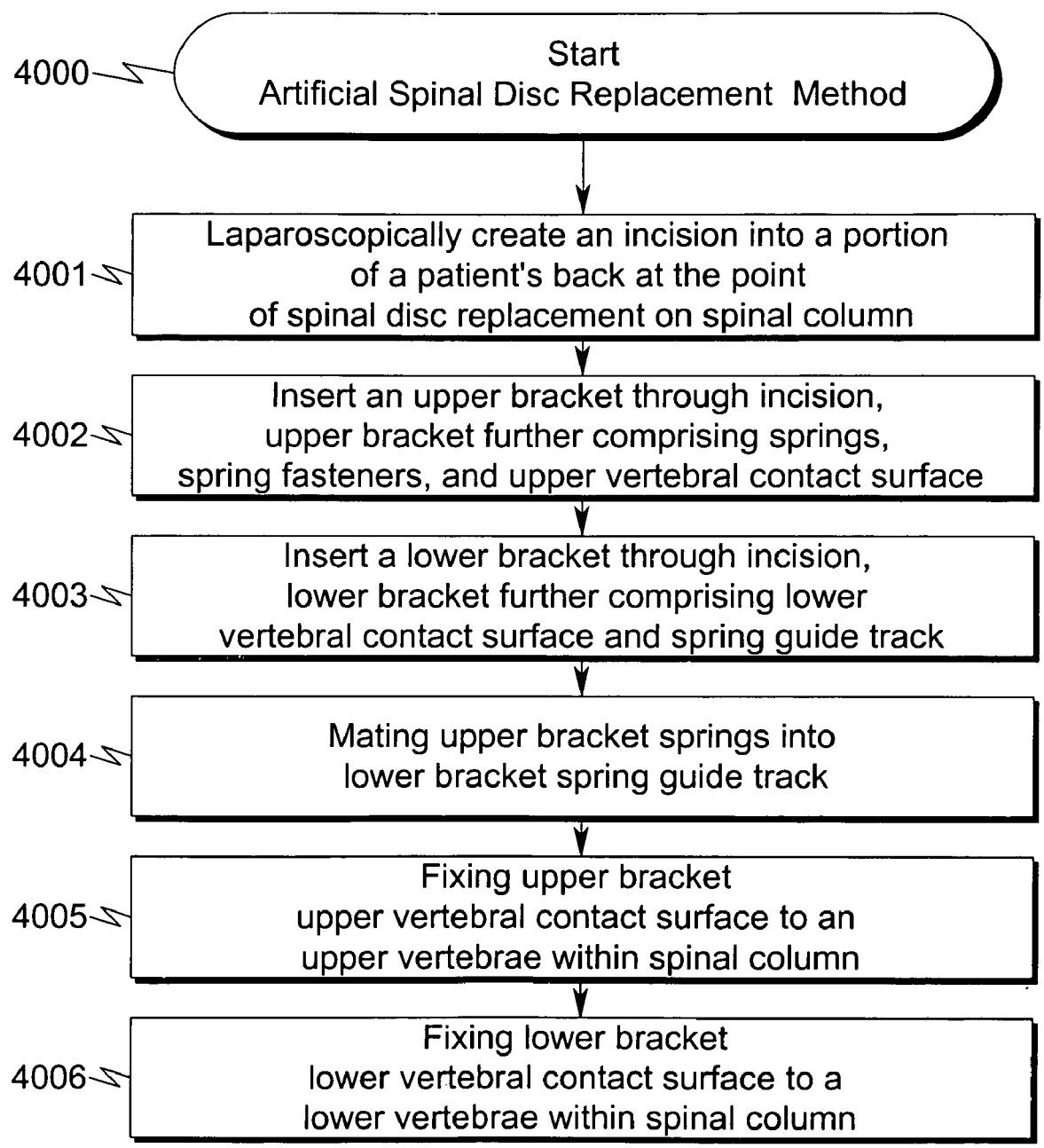
FIG. 40 illustrates a preferred exemplary method embodiment of a surgical procedure useful in installing some embodiments of the present invention.

The exemplary embodiments illustrated herein contain an exemplary spring structure which may be effective in many applications. However, this particular spring structure is not limitive as to the range of spring structures which may be applicable and taught by the present invention. For example, one alternate spring structure is illustrated in FIG. 39 (3900). While the spring structure illustrated in FIG. 39 (3900) does not contain any mounting hole, one skilled in the art will recognize that this (or other spring structures detailed herein) could be augmented with a wide variety of mounting holes and/or studs to permit fastening to the upper bracket. One skilled in the art will recognize that a wide variety of other spring structures may be applied to the teachings of the present invention.

Additionally, note that there is no absolute requirement within the teachings of the present invention that there is more than one spring structure within the replacement disc. One skilled in the art will recognize that the structure illustrated in FIG. 39 (3900) could be fabricated in an arcuate (arc/curved) fashion to mate within the confines of a spring guide track (having one or more cavities) that is machined within the lower bracket. This configuration may include a "wave" style spring structure as illustrated in FIG. 39 (3900), and may include multiple peaks/valleys to ensure the proper spring resistance, contact surface area, and other wear factors required for the application. While a three-peak example is illustrated in FIG. 39 (3900) (and this example does not contain any modification to accommodate the circumferential nature of the spring guide track), one skilled in the art will recognize that these modifications are easily made to the structure of FIG. 39 (3900) to accommodate a singular spring structure if so desired.

Therefore, the term "spring" as used herein should be given its broadest applicable definition consistent with the application to spinal disc replacement. Generally, any material capable of reflexive deformation (with some degree of recovery) would fit this definition. As such, any material subject to Hooke's Law would be a potential candidate for application in the teachings of the present invention.

Laparoscopic Surgical Installation

Figure 3:
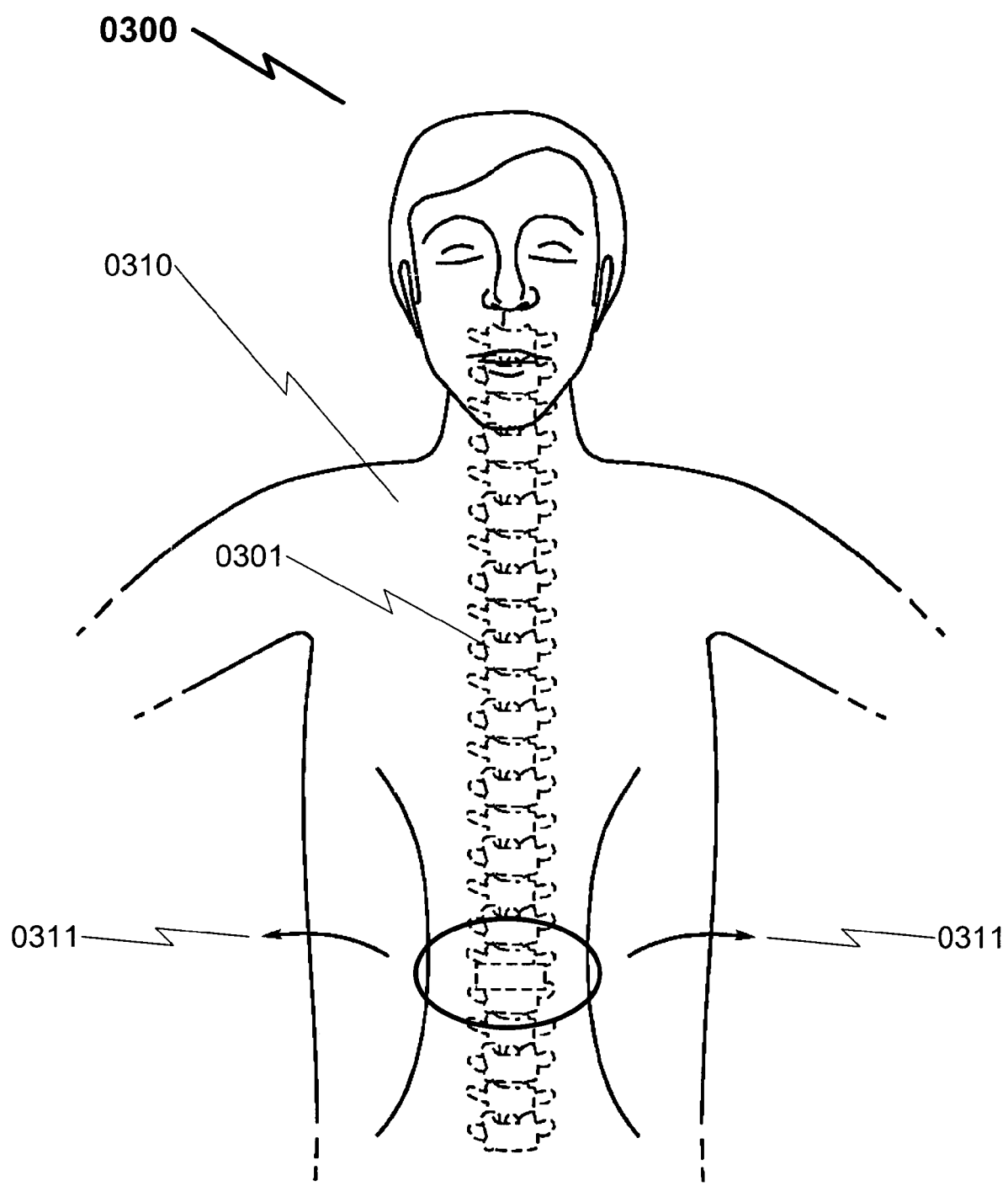
FIG. 3 illustrates a typical surgical procedure associated with prior art embodiments of artificial spinal disc implants.

One of the most significant features of the present invention not available in the prior art is that the present invention spinal disc replacement may be installed through laparoscopic surgery. As illustrated in FIG. 3 (0300), the prior art teaches that a spinal disc replacement requires the "gutting" of the patient from the front side of the abdomen, cutting of muscle, and spreading of organs to access the spine from the front of the patient.

Figure 4:
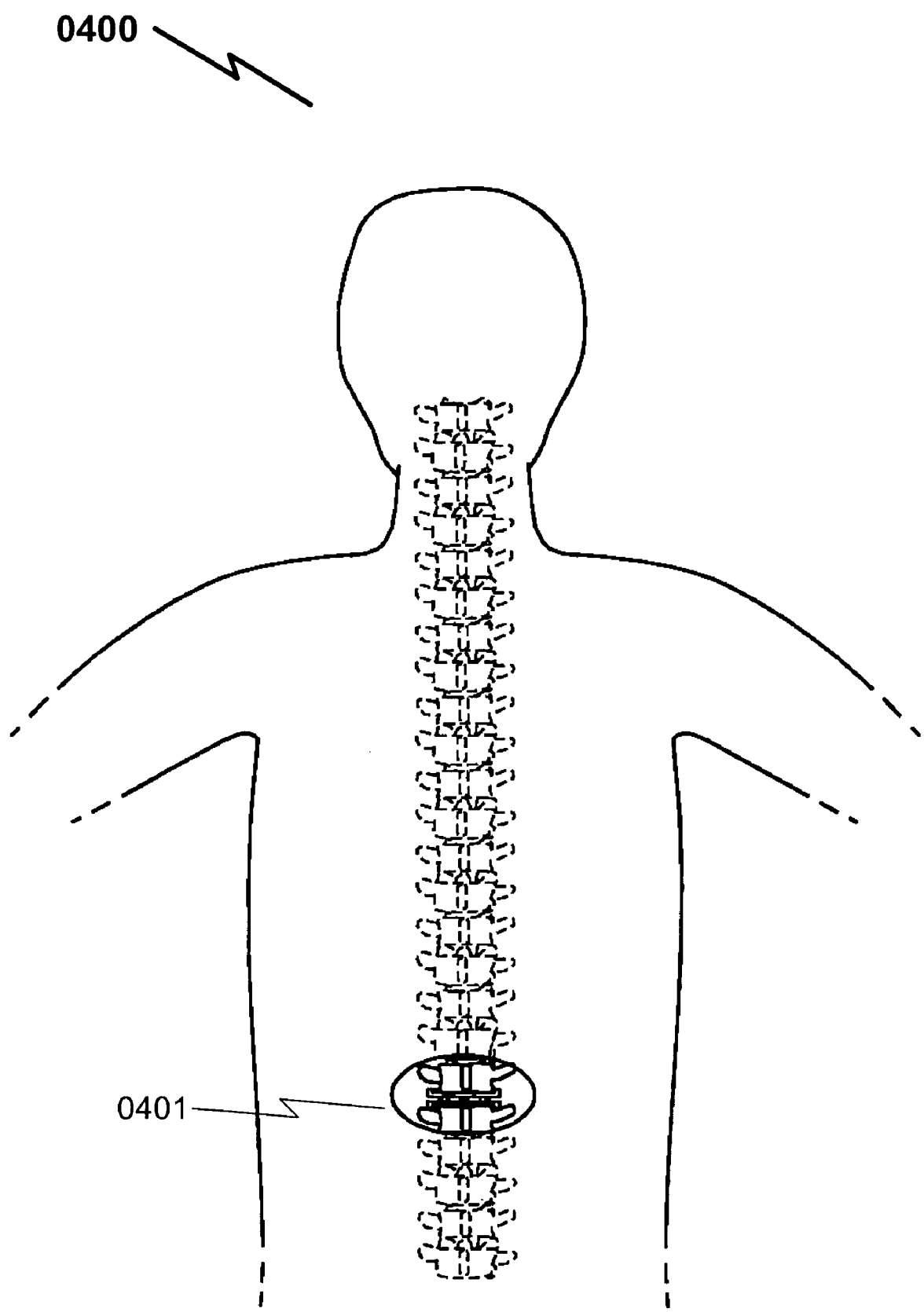
FIG. 4 illustrates a preferred exemplary embodiment of the present invention.
Figure 5:
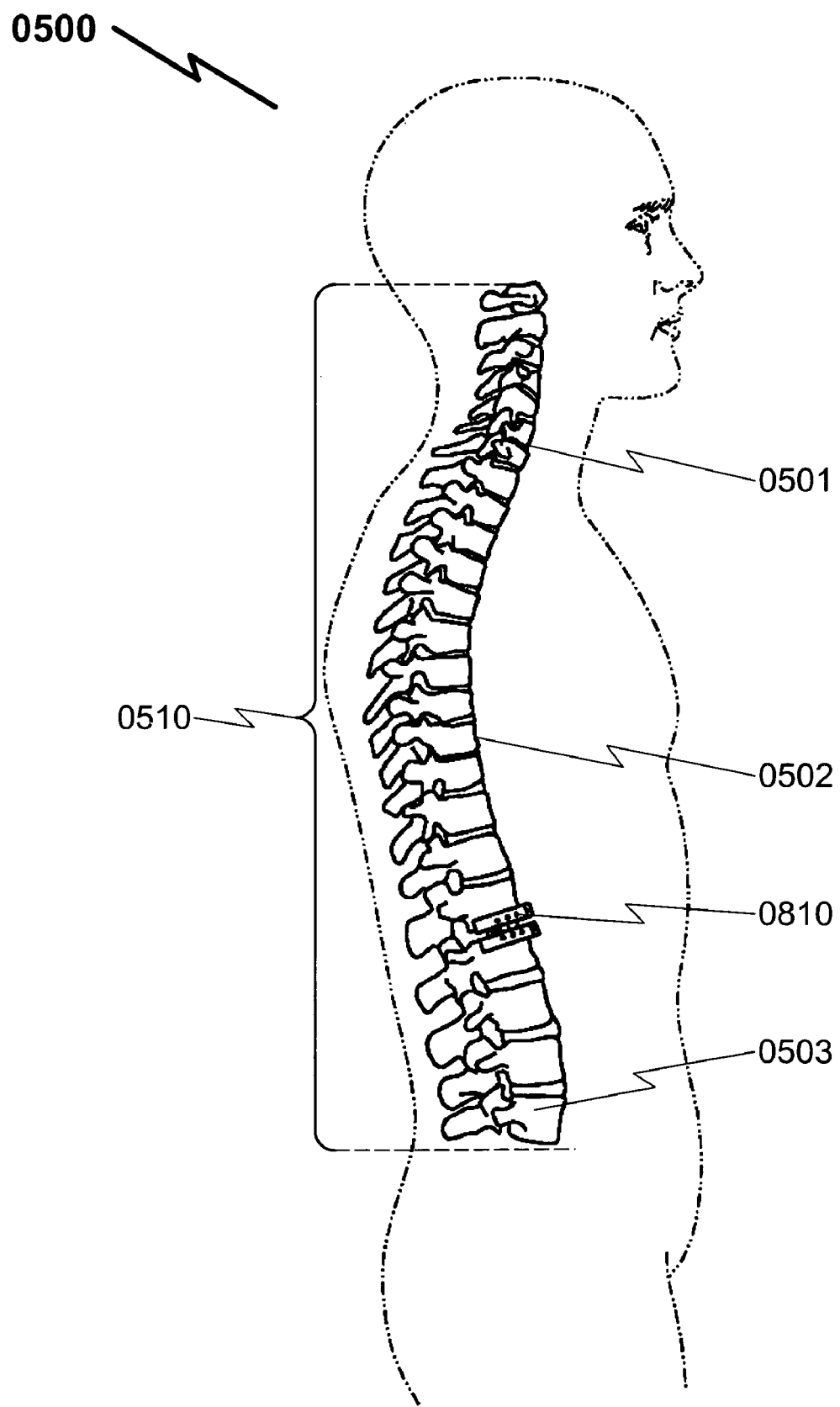
FIG. 5 illustrates a typical laparoscopic surgical procedure associated with some preferred embodiments of the present invention.
Figure 6:
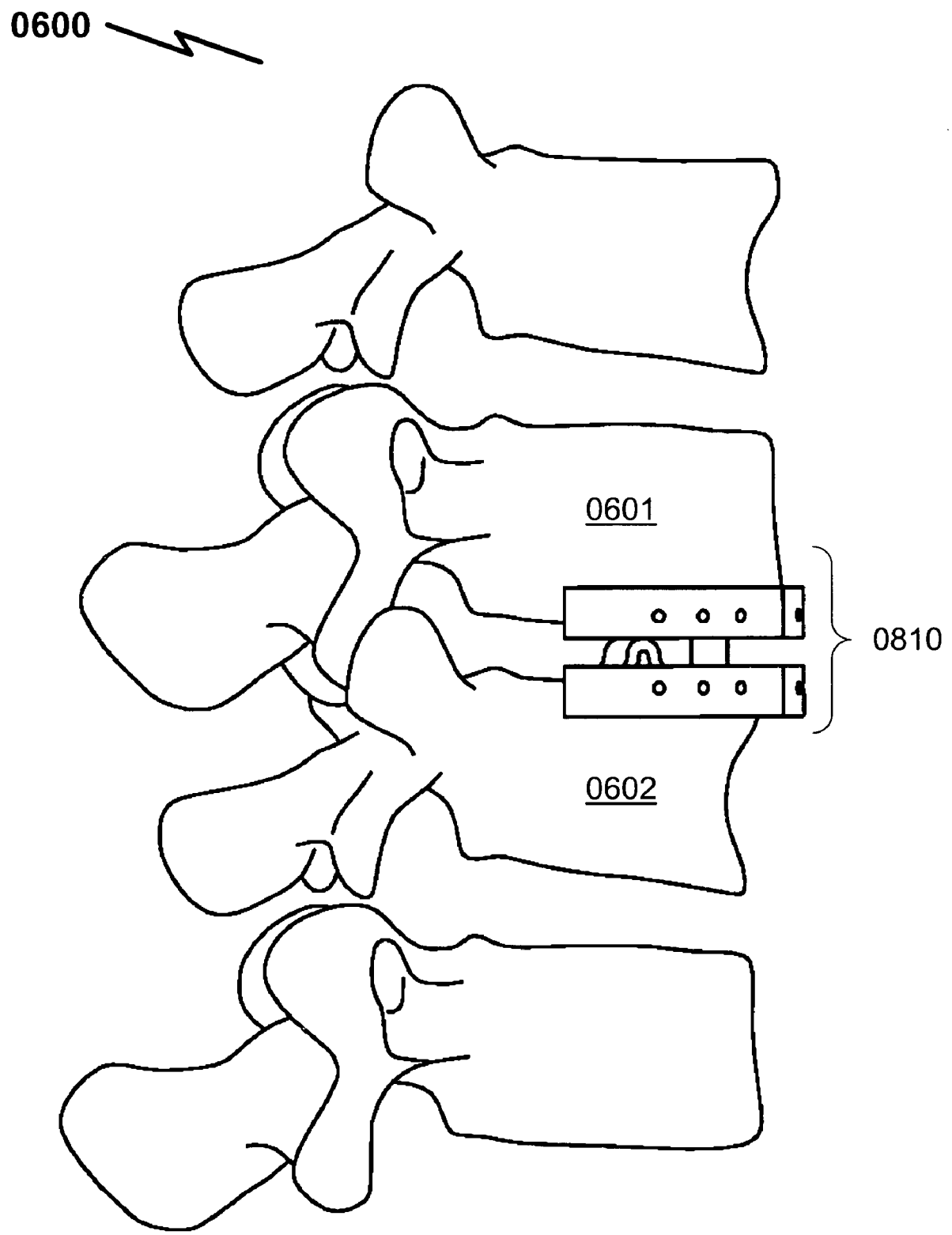
FIG. 6 illustrates a typical spinal disc placement procedures associated with some preferred exemplary embodiments of the present invention.
Figure 7:
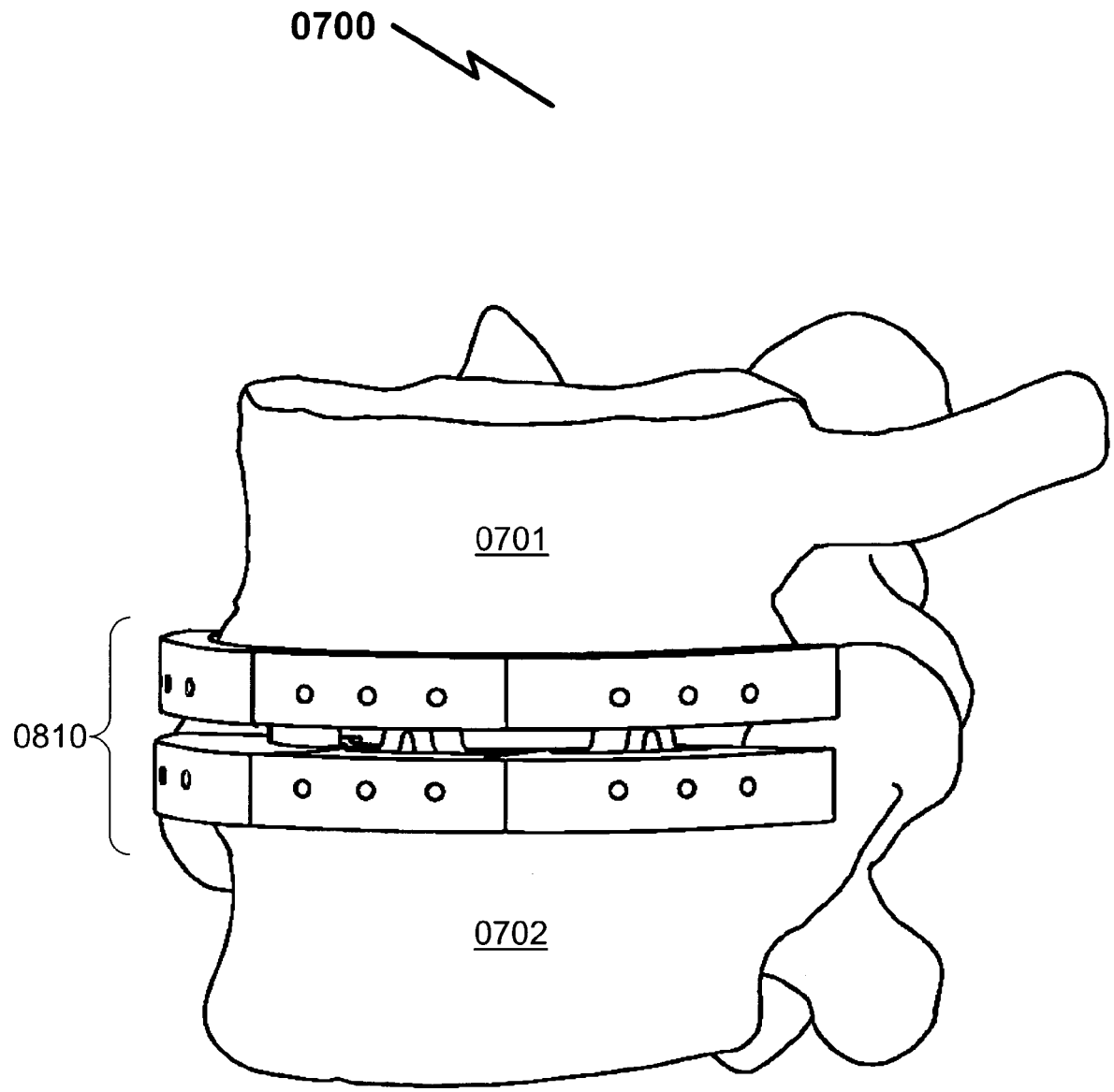
FIG. 7 illustrates a side view of a preferred exemplary embodiment of the present invention as typically installed between two spinal vertebrae.

In contrast, as illustrated in FIG. 4 (0400), the present invention teaches that the disclosed spinal disc replacement may be performed laparoscopically from the back side of the patient. By using special instrumentation and scopes, laparoscopic spinal surgery requires only a small incision. There are numerous benefits of this minimally invasive surgery versus surgical incisions made with traditional fusion surgery. The most significant benefit is a reduced hospital stay and reduced recuperation time.

System Variations

No screws will be needed for implantation or stabilization of this device. However there is a pseudo-screw portion that is angled and fits into the spring at the same angle. The spring fits inside the bottom bracket in a glide section, the bottom bracket is recessed so that the spring fits deeply into the bottom bracket and is adjustable for ROM. The spring guide is wider than the spring itself. The connection slot is beveled and is adjustable dependent on the later and forward motion needed/allowed. The bottom and top brackets are inclined to meet the vertebral body surface on both sides, The undersurface of the brackets are textured to allow maximal attachment surface area to the bone when the residual space is filled with bone glue. There is a hole in the top and bottom plate of the brackets to allow for a needle insertion to squirt the adhesive into the residual space. There are three plates in the bracket that are jig-sawed (interlocked) together during implantation to ease the operative procedure.

The present invention anticipates a wide variety of variations in the basic theme of construction. The examples presented previously do not represent the entire scope of possible usages. They are meant to cite a few of the almost limitless possibilities.

Generalized Method Embodiment (4000)

The present invention may incorporate a method of using the system as described in an application wherein a spinal disc is replaced within a patient. This method (4000) may be generally described as follows:

A method of artificial spinal disc replacement within a patient's spinal column, said method comprising:
(1) Laparoscopically creating an incision into a portion of said patient's back at the point of spinal disc replacement on said spinal column (4001);
(2) Inserting an upper bracket through said incision, said upper bracket further comprising springs, spring fasteners, and upper vertebral contact surface (4002);
(3) Inserting a lower bracket through said incision, said lower bracket further comprising lower vertebral contact surface and spring guide track (4003);
(4) Mating said upper bracket springs into said lower bracket spring guide track (4004);
(5) Fixing said upper bracket upper vertebral contact surface to an upper vertebrae within said spinal column (4005);
(6) Fixing said lower bracket lower vertebral contact surface to a lower vertebrae within said spinal column (4006).

This method may be augmented and/or modified according to variations in the artificial spinal disc replacement system as described above, and specifically anticipates installation of the spinal disc replacement in sections.

CONCLUSION

An artificial spinal disc implant method for intervertebral disc replacement (0810) is disclosed which is formed from an upper (0801) and lower (0802) bracket which mate to upper and lower spinal vertebrae via upper (0831) and lower (0832) vertebral contact surfaces on the upper (0801) and lower (0802) brackets. The upper (0801) and lower (0802) brackets are joined together via springs (0811) connected to the upper bracket (0801) which rest in spring guide tracks (0812) on the lower bracket. The springs (0811) are connected to the upper bracket (0801) via the use of spring fasteners (0821, 0822). The upper (0801) and lower (0802) brackets may be installed in sections (0851, 0861, 0871, 0852, 0862, 0872) using laparoscopic surgical techniques and are attached to upper/lower spinal vertebrae respectively via adhesive means applied using injection holes/ports (0841, 0842) in the upper (0801) and lower (0802) brackets respectively.

The disclosed spinal disc replacement system provides for pivotal and rotational movement, thereby preserving full range-of-motion (ROM) in the patient.

Although a preferred embodiment of the present invention has been illustrated in the accompanying drawings and described in the foregoing Detailed Description, it will be understood that the invention is not limited to the embodiments disclosed, but is capable of numerous rearrangements, modifications, and substitutions without departing from the spirit of the invention as set forth and defined by the following claims.

What is claimed is:

1. A method of artificial spinal disc replacement within a patient's spinal column comprising the steps of:
   (1) providing an, artificial spinal disc system comprising:
      1) Upper bracket further comprising a U-shaped spring, spring fastener, and upper vertebral contact surface; and
      2) Lower bracket further comprising lower vertebral contact surface and spring guide track; wherein
      said upper bracket and said spring are connected to each other via said spring fastener;
      said lower vertebral contact surface defines a first plane;
      said spring guide track comprises a recessed groove extending along said lower vertebral contact surface having a concave wall and a convex wall, where said concave wall is spaced directly opposite said convex wall, wherein said spring rests and is permitted to slide within the peripheral boundaries of said spring guide track along a direction parallel to said first plane; and
      said recessed groove protrudes from said lower vertebral contact surface which contains the ends of said spring and has a flat bottom that is beveled on either side;
   (2) Laparoscopically creating an incision into a portion of said patient's back at the point of spinal disc replacement on said spinal column;
   (3) Inserting said upper bracket through said incision;
   (4) Inserting said lower bracket through said incision;
   (5) Mating said upper bracket spring into said lower bracket spring guide track;
   (6) Fixing said upper bracket upper vertebral contact surface to an upper vertebrae within said spinal column;
   (7) Fixing said lower bracket lower vertebral contact surface to a lower vertebrae within said spinal column.

2. The artificial spinal disc replacement method of claim 1 wherein said attachment of said upper bracket to said upper spinal vertebrae is via adhesive.

3. The artificial spinal disc replacement method of claim 1 wherein said attachment of said upper bracket to said upper spinal vertebrae is via bone glue.

4. The artificial spinal disc replacement method of claim 1 wherein said upper bracket further comprises injection holes/ports for adhesive.

5. The artificial spinal disc replacement method of claim 1 wherein said attachment of said lower bracket to said lower spinal vertebrae is via adhesive.

6. The artificial spinal disc replacement method of claim 1 wherein said attachment of said lower bracket to said lower spinal vertebrae is via bone glue.

7. The artificial spinal disc replacement method of claim 1 wherein said lower bracket further comprises injection holes/ports for adhesive.

8. The artificial spinal disc replacement method of claim 1 wherein said upper bracket, said spring, and said spring fastener are integrated into a single unitary structure.

9. The artificial spinal disc replacement method of claim 1 wherein said spring fastener further comprises a machine screw and acorn nut.

10. The artificial spinal disc replacement method of claim 1 wherein said spring fastener further comprises a rivet.

11. The artificial spinal disc replacement method of claim 1 wherein said spring fastener further comprises cylindrical threaded projections and fastening nuts.

12. The artificial spinal disc replacement method of claim 1 wherein said upper bracket comprises a plurality of springs.

13. The artificial spinal disc replacement method of claim 1 wherein said lower bracket comprises a plurality of spring guide tracks.

14. The artificial spinal disc replacement method of claim 1 said upper bracket comprises a plurality of sections.

15. The artificial spinal disc replacement method of claim 1 said lower bracket comprises a plurality of sections.

16. The artificial spinal disc replacement method of claim 1 said upper bracket and said lower bracket are co-planar.

17. The artificial spinal disc replacement method of claim 1 said upper bracket is non-co-planar.

18. The artificial spinal disc replacement method of claim 1 said lower bracket is non-co-planar.

19. The artificial spinal disc replacement method of claim 1 said upper vertebral contact surface is surface conditioned to promote adhesion to said upper spinal vertebrae and said lower vertebral contact surface is surface conditioned to promote adhesion to said lower spinal vertebrae.

* * * * *